(12) United States Patent
Yellin et al.

(10) Patent No.: US 11,571,307 B2
(45) Date of Patent: Feb. 7, 2023

(54) METHODS, DEVICES, AND SYSTEMS FOR PERCUTANEOUSLY ANCHORING ANNULOPLASTY RINGS

(71) Applicant: VALCARE, INC., Newport Beach, CA (US)

(72) Inventors: Nadav Yellin, Ramat Gan (IL); Samuel M. Shaolian, Newport Beach, CA (US); Jeffrey P. Dumontelle, Irvine, CA (US)

(73) Assignee: VALCARE, INC., Herzelyia Pituach (IL)

( * ) Notice: Subject to any disclaimer, the term of this patent is extended or adjusted under 35 U.S.C. 154(b) by 435 days.

(21) Appl. No.: 16/939,933

(22) Filed: Jul. 27, 2020

(65) Prior Publication Data
US 2021/0085463 A1 Mar. 25, 2021

Related U.S. Application Data

(60) Continuation of application No. 15/810,936, filed on Nov. 13, 2017, now Pat. No. 10,722,363, which is a
(Continued)

(51) Int. Cl.
*A61F 2/24* (2006.01)

(52) U.S. Cl.
CPC .......... *A61F 2/2466* (2013.01); *A61F 2/2427* (2013.01); *A61F 2/2448* (2013.01); *A61F 2220/0016* (2013.01)

(58) Field of Classification Search
CPC .... A61F 2/2466; A61F 2/2427; A61F 2/2448; A61F 2220/0016; A61F 2/2442;
(Continued)

(56) References Cited

U.S. PATENT DOCUMENTS

| 4,602,911 A | 7/1986 | Ahmadi et al. |
| 5,236,440 A | 8/1993 | Hlavacek |

(Continued)

FOREIGN PATENT DOCUMENTS

| DE | 102014102653 A1 | 9/2015 |
| EP | 1752115 A1 | 2/2007 |

(Continued)

OTHER PUBLICATIONS

European Search Report in EP 17155803.4 dated Aug. 9, 2017.
(Continued)

*Primary Examiner* — Robert A Lynch
*Assistant Examiner* — Mikail A Mannan
(74) *Attorney, Agent, or Firm* — Dorsey & Whitney LLP

(57) ABSTRACT

Apparatus, systems, and methods are provided for percutaneous transcatheter delivery and fixation of annuloplasty rings to heart valves. An annuloplasty ring includes an outer tube, an inner body member, and an anchor deployment system. The outer tube includes a plurality of windows and has an axis along its length. The internal body member includes a plurality of anchors formed perpendicular to the axis. The anchor deployment system selectively rotates the internal body member with respect to the axis of the outer tube. The rotation deploys the plurality of anchors through the plurality of windows.

19 Claims, 27 Drawing Sheets

Related U.S. Application Data continuation of application No. 14/886,175, filed on Oct. 19, 2015, now Pat. No. 9,814,576, which is a division of application No. 13/799,642, filed on Mar. 13, 2013, now Pat. No. 9,180,008, which is a continuation-in-part of application No. 13/779,478, filed on Feb. 27, 2013, now Pat. No. 9,839,519.

(60) Provisional application No. 61/734,904, filed on Dec. 7, 2012, provisional application No. 61/604,856, filed on Feb. 29, 2012.

(58) Field of Classification Search
CPC .... A61F 2/2451; A61F 2/2454; A61F 2/2457; A61F 2/2409; A61F 2/2445; A61F 2/243; A61B 2017/00783; A61B 2017/00243
See application file for complete search history.

(56) References Cited

U.S. PATENT DOCUMENTS

| | | |
|---|---|---|
| 5,306,296 A | 4/1994 | Wright et al. |
| 5,695,518 A | 12/1997 | Laerum |
| 5,716,370 A | 2/1998 | Williamson, IV et al. |
| 5,855,614 A | 1/1999 | Stevens et al. |
| 6,113,611 A | 9/2000 | Allen et al. |
| 6,231,602 B1 | 5/2001 | Carpentier et al. |
| 6,619,291 B2 | 9/2003 | Hlavka et al. |
| 6,629,534 B1 | 10/2003 | St. Goar et al. |
| 6,669,687 B1 | 12/2003 | Saadat |
| 6,689,048 B2 | 2/2004 | Vanden Hoek et al. |
| 6,726,704 B1 | 4/2004 | Loshakove et al. |
| 6,776,784 B2 | 8/2004 | Ginn |
| 6,790,229 B1 | 9/2004 | Berreklouw |
| 6,797,002 B2 | 9/2004 | Spence et al. |
| 6,805,711 B2 | 10/2004 | Quijano et al. |
| 6,893,459 B1 | 5/2005 | Macoviak |
| 7,101,395 B2 | 9/2006 | Tremulis et al. |
| 7,114,953 B1 | 10/2006 | Wagner |
| 7,175,660 B2 | 2/2007 | Cartledge et al. |
| 7,238,191 B2 | 7/2007 | Bachmann |
| 7,285,087 B2 | 10/2007 | Moaddeb et al. |
| 7,297,150 B2 | 11/2007 | Cartledge et al. |
| 7,569,072 B2 | 8/2009 | Berg et al. |
| 7,594,887 B2 | 9/2009 | Moaddeb et al. |
| 7,635,329 B2 | 12/2009 | Goldfarb et al. |
| 7,655,040 B2 | 2/2010 | Douk et al. |
| 7,717,954 B2 | 5/2010 | Solem et al. |
| 7,722,668 B2 | 5/2010 | Moaddeb et al. |
| 7,758,637 B2 | 7/2010 | Starksen et al. |
| 7,837,729 B2 | 11/2010 | Gordon et al. |
| 7,988,725 B2 | 8/2011 | Gross et al. |
| 8,163,014 B2 | 4/2012 | Lane et al. |
| 8,182,529 B2 | 5/2012 | Gordon et al. |
| 8,236,049 B2 | 8/2012 | Rowe et al. |
| 8,287,591 B2 | 10/2012 | Keidar et al. |
| 8,518,107 B2 | 8/2013 | Tsukashima et al. |
| 8,579,968 B1 | 11/2013 | Shannon et al. |
| 9,180,008 B2 | 11/2015 | Yellin et al. |
| 9,839,519 B2 | 12/2017 | Shaolian et al. |
| 11,298,230 B2 | 4/2022 | Shaolian et al. |
| 2002/0151961 A1 | 10/2002 | Lashinski et al. |
| 2002/0151970 A1 | 10/2002 | Garrison et al. |
| 2002/0188170 A1 | 12/2002 | Santamore et al. |
| 2002/0198526 A1 | 12/2002 | Shaolian et al. |
| 2003/0050693 A1 | 3/2003 | Quijano et al. |
| 2003/0078465 A1 | 4/2003 | Pai et al. |
| 2003/0078671 A1 | 4/2003 | Lesniak et al. |
| 2003/0191528 A1 | 10/2003 | Quijano et al. |
| 2003/0198605 A1 | 10/2003 | Montgomery |
| 2003/0199974 A1 | 10/2003 | Lee et al. |
| 2004/0044364 A1 | 3/2004 | DeVries et al. |
| 2004/0068276 A1 | 4/2004 | Golden et al. |
| 2004/0122514 A1 | 6/2004 | Fogarty et al. |
| 2004/0138744 A1 | 7/2004 | Lashinski et al. |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0249391 A1 | 12/2004 | Cummins |
| 2004/0260393 A1 | 12/2004 | Rahdert et al. |
| 2004/0260394 A1 | 12/2004 | Douk et al. |
| 2005/0020696 A1 | 1/2005 | Montgomery et al. |
| 2005/0033325 A1 | 2/2005 | May et al. |
| 2005/0065550 A1 | 3/2005 | Starksen et al. |
| 2005/0090846 A1 | 4/2005 | Pedersen et al. |
| 2005/0096740 A1 | 5/2005 | Langberg et al. |
| 2005/0113910 A1 | 5/2005 | Paniagua et al. |
| 2005/0137692 A1 | 6/2005 | Haug et al. |
| 2005/0137695 A1 | 6/2005 | Salahieh et al. |
| 2005/0203549 A1 | 9/2005 | Realyvasquez |
| 2005/0222678 A1 | 10/2005 | Lashinski et al. |
| 2005/0240200 A1 | 10/2005 | Bergheim |
| 2005/0267572 A1 | 12/2005 | Schoon et al. |
| 2005/0283190 A1 | 12/2005 | Huitema et al. |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0020327 A1 | 1/2006 | Lashinski et al. |
| 2006/0129025 A1 | 6/2006 | Levine et al. |
| 2006/0155165 A1 | 7/2006 | Vanden Hoek et al. |
| 2006/0161169 A1 | 7/2006 | Nieminen et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0195183 A1 | 8/2006 | Navia et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk |
| 2007/0038296 A1 | 2/2007 | Navia et al. |
| 2007/0051377 A1 | 3/2007 | Douk et al. |
| 2007/0067027 A1 | 3/2007 | Moaddeb et al. |
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1 | 9/2007 | Webler et al. |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0306586 A1 | 12/2008 | Cartledge et al. |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0211166 A1 | 8/2010 | Miller et al. |
| 2010/0249920 A1 | 9/2010 | Bolling et al. |
| 2010/0266989 A1 | 10/2010 | Piergallini et al. |
| 2010/0280604 A1 | 11/2010 | Zipory et al. |
| 2010/0280605 A1 | 11/2010 | Hammer et al. |

(56) References Cited

U.S. PATENT DOCUMENTS

| | | |
|---|---|---|
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2012/0022557 A1 | 1/2012 | Cabiri et al. |
| 2012/0022644 A1 | 1/2012 | Reich et al. |
| 2012/0059458 A1 | 3/2012 | Buchbinder et al. |
| 2012/0095455 A1 | 4/2012 | Rodmond et al. |
| 2012/0123531 A1* | 5/2012 | Tsukashima .......... A61F 2/2448 623/2.37 |
| 2012/0136436 A1 | 5/2012 | Cabiri et al. |
| 2012/0165930 A1 | 6/2012 | Gifford, III et al. |
| 2012/0245604 A1 | 9/2012 | Tegzes |
| 2012/0310330 A1 | 12/2012 | Buchbinder et al. |
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2015/0173897 A1 | 6/2015 | Raanani et al. |
| 2015/0173987 A1 | 6/2015 | Albinmousa et al. |
| 2015/0351903 A1 | 12/2015 | Morriss et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0106420 A1 | 4/2016 | Foerster et al. |
| 2016/0120642 A1 | 5/2016 | Shaolian et al. |
| 2016/0120645 A1 | 5/2016 | Alon |
| 2016/0331534 A1 | 11/2016 | Buchbinder et al. |
| 2017/0042670 A1 | 2/2017 | Shaolian et al. |
| 2017/0231763 A1 | 8/2017 | Yellin |
| 2018/0042723 A1 | 2/2018 | Yellin et al. |
| 2018/0161160 A1 | 6/2018 | Shaolian et al. |
| 2018/0161161 A1 | 6/2018 | Yellin et al. |
| 2019/0083240 A1 | 3/2019 | Shaolian et al. |
| 2019/0133765 A1 | 5/2019 | Yellin et al. |

FOREIGN PATENT DOCUMENTS

| | | |
|---|---|---|
| EP | 2600799 A2 | 6/2013 |
| EP | 2967700 A1 | 1/2016 |
| KR | 1020040095482 A | 11/2004 |
| RU | 125062 U1 | 2/2013 |
| WO | 9009153 A1 | 8/1990 |
| WO | 03017874 A1 | 3/2003 |
| WO | 03047467 A1 | 6/2003 |
| WO | 2003047467 A1 | 6/2003 |
| WO | 2005046488 A2 | 5/2005 |
| WO | 2009052427 A1 | 4/2009 |
| WO | 2009120764 A2 | 10/2009 |
| WO | 2010004546 A1 | 1/2010 |
| WO | 2010085659 A1 | 7/2010 |
| WO | 2011011443 A2 | 1/2011 |
| WO | 2011097355 A2 | 8/2011 |
| WO | 2011154942 A2 | 12/2011 |
| WO | 2012004679 A2 | 1/2012 |
| WO | 2012019052 A2 | 2/2012 |
| WO | 2012040865 A1 | 4/2012 |
| WO | 2012063228 A1 | 5/2012 |
| WO | 2012095159 A2 | 7/2012 |
| WO | 2012106354 A1 | 8/2012 |
| WO | 2012167095 A2 | 12/2012 |
| WO | 2013095816 A1 | 6/2013 |
| WO | 2013128436 A1 | 9/2013 |
| WO | 2013130641 A1 | 9/2013 |
| WO | 2013175468 A2 | 11/2013 |
| WO | 2014089424 A1 | 6/2014 |
| WO | 2014145399 A1 | 9/2014 |
| WO | 2014189509 A1 | 11/2014 |
| WO | 2014190329 A1 | 11/2014 |
| WO | 2014210600 A2 | 12/2014 |
| WO | 2015132668 A1 | 9/2015 |
| WO | 2018035118 A1 | 2/2018 |

OTHER PUBLICATIONS

International Search Report and Written Opinion for PCT/US2011/046659 dated Jun. 4, 2012.
International Search Report and Written Opinion for PCT/US2012/040481 dated Dec. 6, 2012.
International Search Report and Written Opinion for PCT/US2013/042275 dated Feb. 20, 2014.
International Search Report and Written Opinion for PCT/US2013/073552 dated Mar. 6, 2014.
International Search Report and Written Opinion for PCT/US2014/030163 dated Aug. 27, 2014.
International Search Report and Written Opinion for PCT/US2014/039454 dated Oct. 22, 2014.
International Search Report and Written Opinion for PCT/US2014/039545 dated Oct. 22, 2014.
International Search Report and Written Opinion for PCT/US2017/046933 dated Dec. 21, 2017.
International Search Report and Written Opinion for PCT2019/064289 dated Feb. 5, 2020.
International Search Report for PCT/US2013/028065 dated Jun. 27, 2013.
International Search Report for PCT/US2013/058102 dated Apr. 21, 2014.
International Search Report for PCT/US2014/044920 dated Dec. 24, 2014.
Lendlein et al., Biodegradable, Elastic Shape-Memory Polymers for Potential Biomedical Applications, Science, vol. 296 (May 31, 2002), pp. 1673-1676.
Supplemental European Search Report and Written Opinion for EP 12793292.9 dated Dec. 1, 2014.
Supplemental European Search Report and Written Opinion for EP 14762806.9 dated Jul. 29, 2016.
Supplementary Partial European Search Report for EP 13755441 dated Nov. 3, 2015.
13860442.6, et al., Extended European Search Report , dated Aug. 11, 2016 ,7 pages.
14801009.3, et al., Extended European Search Report , dated Dec. 5, 2016 ,8 pages.
19151726.7, et al., Extended European Search Report , dated Jul. 22, 2019 ,9 pages.
PCT/US2018/022910, et al., International Search Report and Written Opinion , dated May 23, 2018 ,6 pages.
PCT/US2019/064289, et al., International Search Report and Written Opinion , dated Feb. 5, 2020.
U.S. Appl. No. 15/838,241, et al., Non-Final Office Action , dated Feb. 18, 2021 ,11 pages.
20209605.3, et al., Extended European Search Report , dated Mar. 9, 2021 ,7 pages.

* cited by examiner

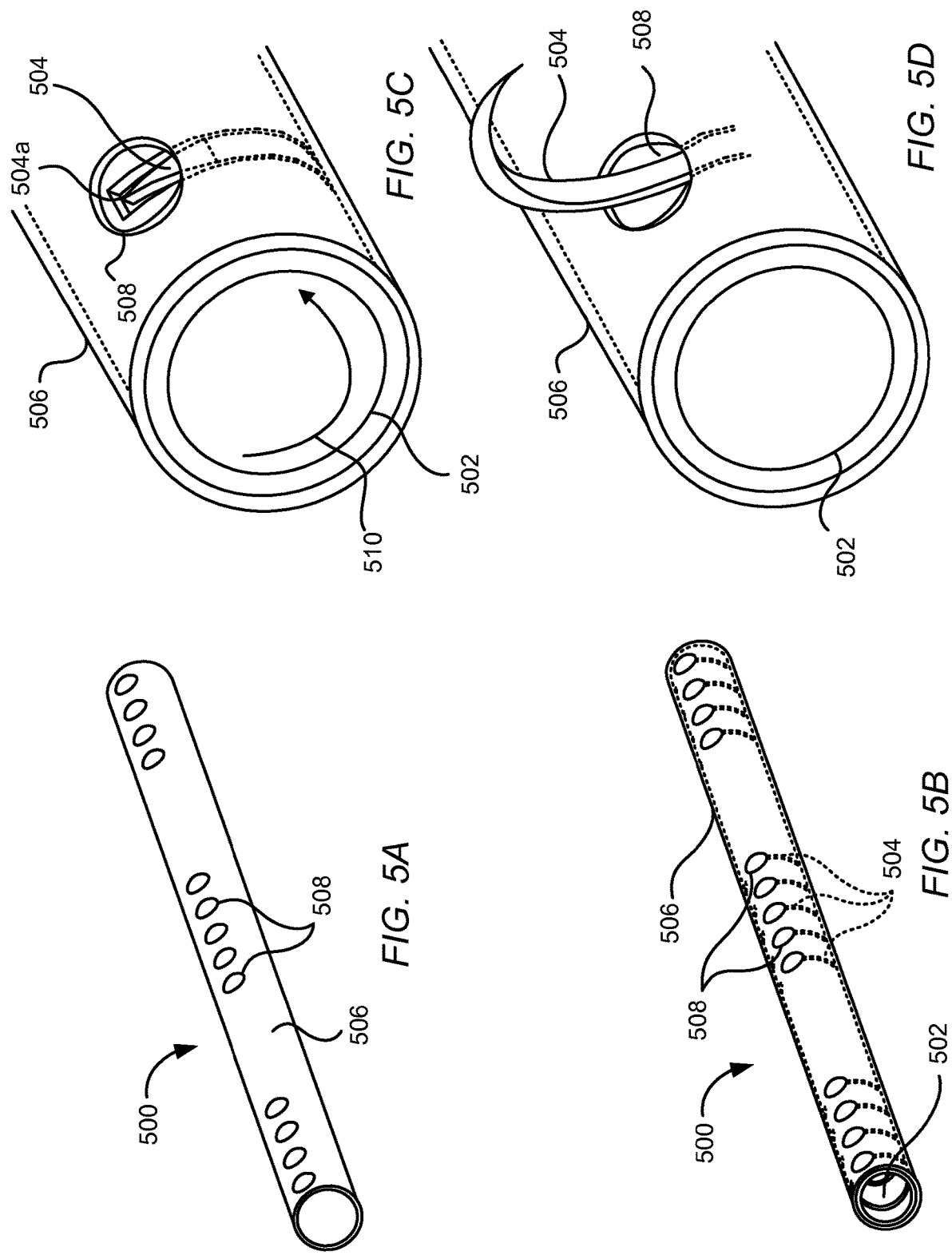

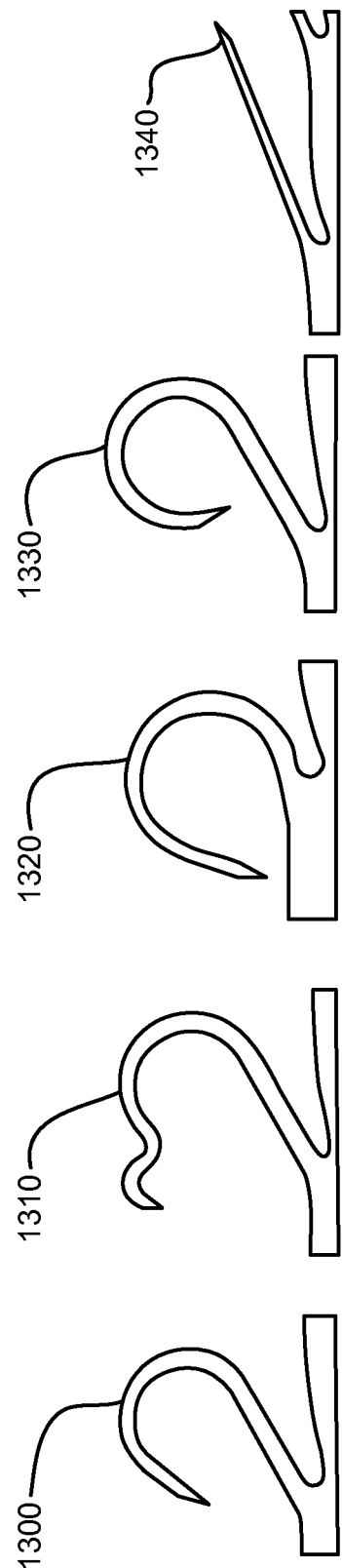

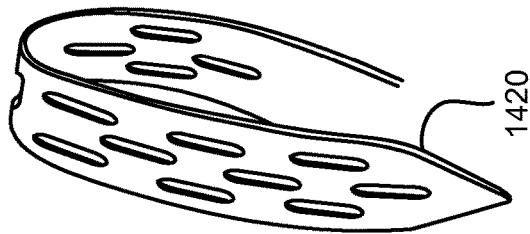
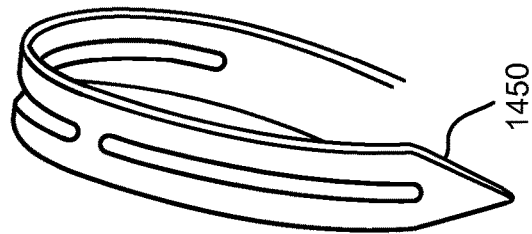
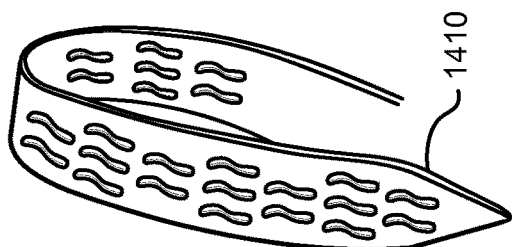
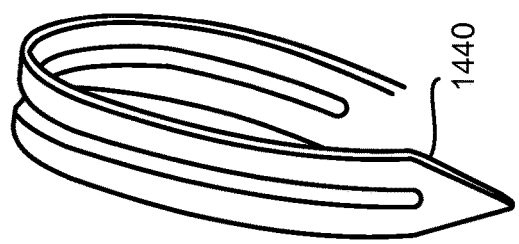
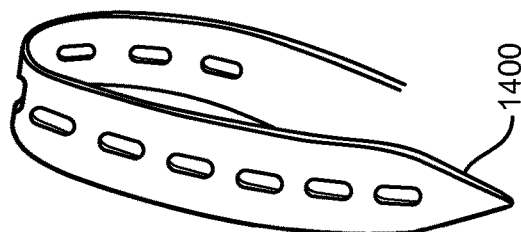
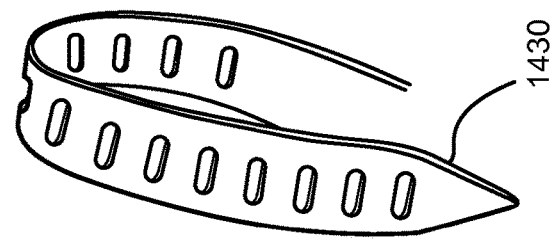
FIG 14

METHODS, DEVICES, AND SYSTEMS FOR PERCUTANEOUSLY ANCHORING ANNULOPLASTY RINGS

RELATED APPLICATIONS

This application claims the benefit under 35 U.S.C. § 119(e) of U.S. Provisional Patent Application No. 61/734,904, filed Dec. 7, 2012, titled "ROTATIONAL BARBS," and is a continuation-in-part of U.S. patent application Ser. No. 13/779,478, filed Feb. 27, 2013, titled "PERCUTANEOUS ANNULOPLASTY SYSTEM WITH ANTERIOR-POSTERIOR ADJUSTMENT," which claims the benefit under 35 U.S.C. § 119(e) of U.S. Provisional Patent Application No. 61/604,856, filed Feb. 29, 2012, titled "PERCUTANEOUS ANNULOPLASTY SYSTEM WITH ANTERIOR POSTERIOR ADJUSTMENT," and of U.S. Provisional Patent Application No. 61/734,904, each of which is hereby incorporated by reference herein in its entirety.

TECHNICAL FIELD

The present disclosure relates to treating and repairing heart valves, and specifically to apparatus, systems, and methods for percutaneous transcatheter repair of heart valves. Disclosed embodiments include adjustable annuloplasty rings that are configured to be delivered through a catheter and percutaneously anchored to a heart valve annulus.

BACKGROUND INFORMATION

Heart valve defects, such as regurgitation, may be caused by a relaxation of the tissue surrounding a heart valve (e.g., the mitral valve or tricuspid valve). This causes the valve opening to enlarge, which prevents the valve from sealing properly. Such heart conditions are commonly treated by a procedure during which an annuloplasty ring is fixed or secured to the annulus of the valve. Cinching or securing the tissue of the annulus to the annuloplasty ring can restore the valve opening to its approximate original size and operating efficiency.

Typically, annuloplasty rings have been implanted during open heart surgery, so that the annuloplasty ring can be sewn into the valve annulus. Open heart surgery is a highly invasive procedure that requires connecting a heart and lung machine (to pump the patient's blood and breathe for the patient), stopping the patient's heart, and cutting open the thoracic cavity and heart organ. The procedure can expose the patient to a high risk of infection and may result in a long and difficult recovery. The recovery can be particularly difficult for patients in less than optimal health due to the effects of suffering from a heart valve defect such as regurgitation.

BRIEF DESCRIPTION OF THE DRAWINGS

FIG. 5A is a perspective view of a retaining cover used in an anchor deployment system according to certain embodiments.

FIG. 5B is a perspective view of a body member within the retaining cover shown in FIG. 5A according to certain embodiments.

FIG. 5C is an enlarged view of the retaining cover of and body member shown in FIG. 5B.

FIG. 5D illustrates the retaining cover shown in FIG. 5C after rotating the body member to deploy an anchor.

FIG. 13 illustrates various anchor shapes that may be used with the disclosed annuloplasty rings according to certain embodiments.

FIG. 14 illustrates various anchor designs that may be used with the disclosed annuloplasty rings according to certain embodiments.

DETAILED DESCRIPTION OF PREFERRED EMBODIMENTS

While there are flexible rings currently on the market, surgeons generally prefer rigid and semi-rigid rings for valve repair to treat ischemic and functional mitral valve regurgitation. Rigid and semi-rigid rings, unfortunately, do not lend themselves to being delivered into the heart through a catheter. The present disclosure provides systems and methods for repairing heart valves through percutaneous transcatheter delivery and fixation of annuloplasty rings to heart valves. The embodiments of annuloplasty rings can be configured in both an elongate insertion geometry that can be inserted into a catheter tube and an operable geometry providing a curved and rigid or semi-rigid annular shape.

In certain embodiments, an annuloplasty ring is delivered percutaneously to the mitral and/or tricuspid valve annulus of the heart. The disclosed embodiments apply, for example, to trans-septal, retrograde, or trans-apical approaches for delivering annuloplasty rings to an annulus of a heart valve. For delivery of rings into the mitral valve, percutaneous delivery may use a retrograde approach from the femoral artery, an antegrade approach via a trans-septal entry, or a trans-apical approach through the base or apex of the heart through the left ventricle to the left atrium. Delivery of rings to the tricuspid valve may include an approach from the inferior or superior vena cava.

Certain annuloplasty rings disclosed herein are small and flexible enough to be percutaneously delivered, but can be put into a rigid or semi-rigid ring shape and then securely anchored into the heart valve annulus without having to open up the chest. Disclosed embodiments include segmented annuloplasty rings, delivery systems, and methods for anchoring and cinching the annuloplasty ring around the valve annulus.

Example Ring Embodiments with Radial, Rotational Anchors

Figure 1A:
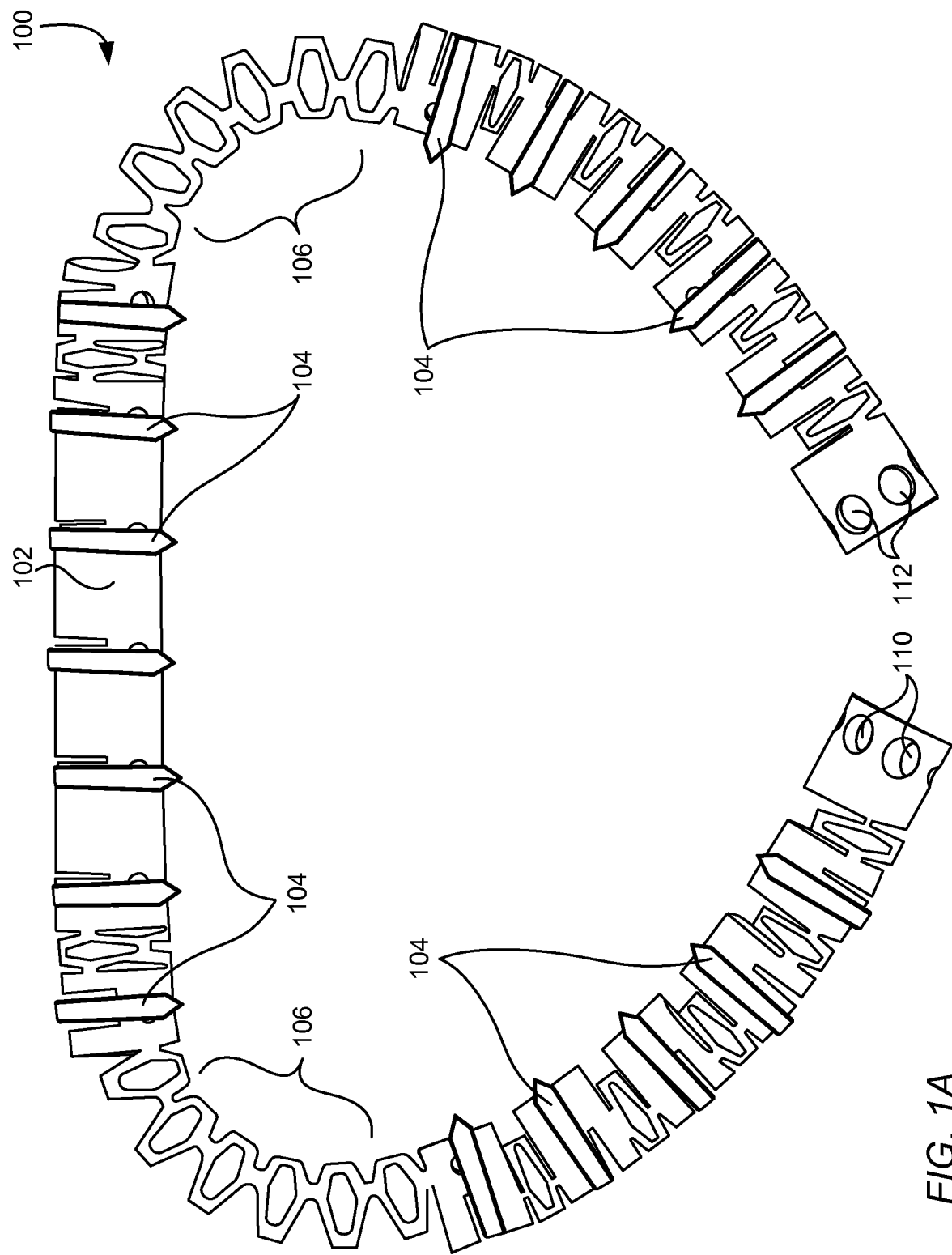
FIG. 1A is a top view an internal body member of an annuloplasty ring in an operative geometry according to certain embodiments.
Figure 1B:
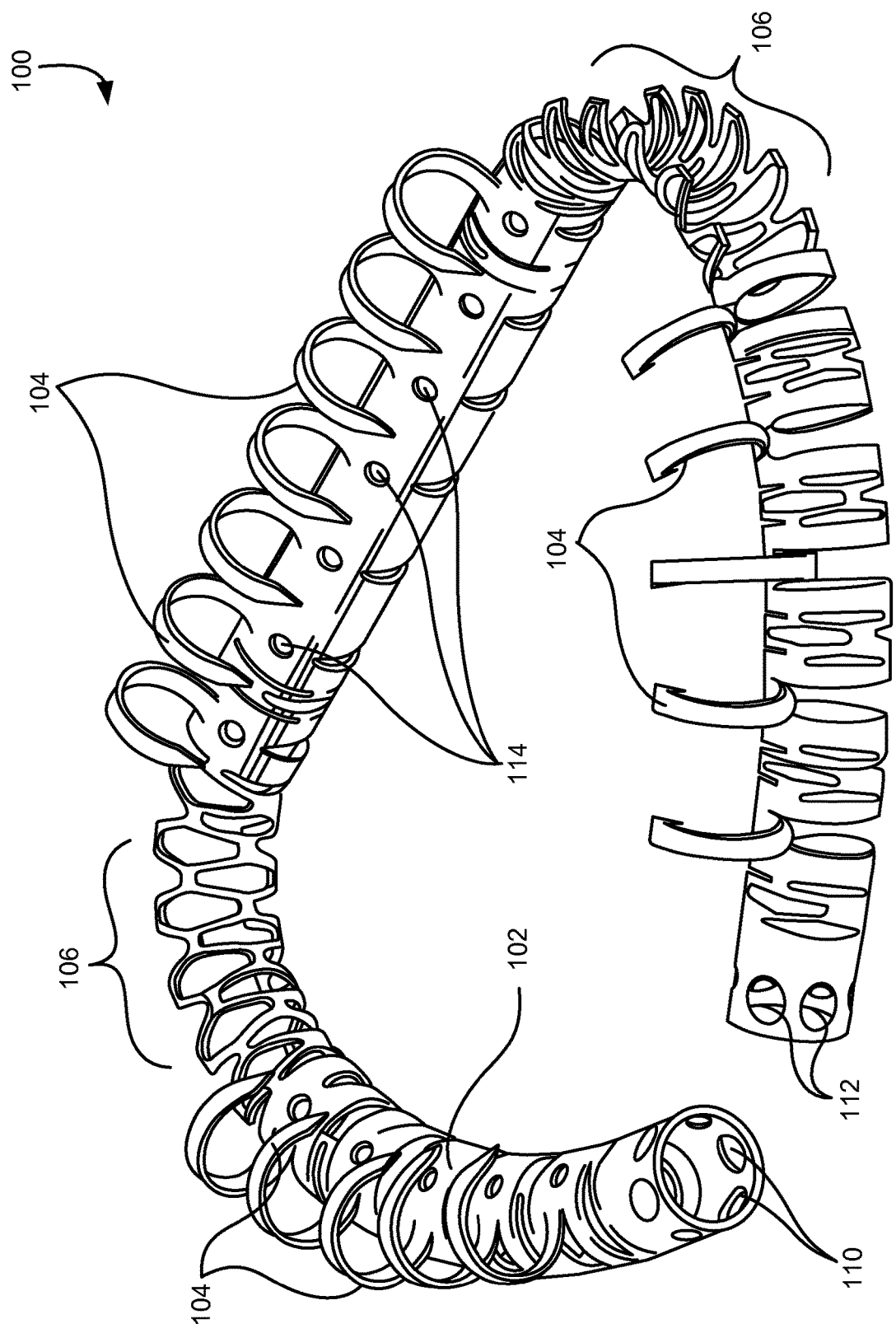
FIG. 1B is a perspective view of the internal body member shown in FIG. 1A.

FIGS. 1A and 1B are top and perspective views, respectively, of an internal body member 100 of an annuloplasty ring in an operative geometry according to certain embodiments. The internal body member 100 includes a hypotube 102 cut to include a plurality of anchors 104 and one or more expansion regions 106. As discussed below, the hypotube 102 may be cut in a pattern (e.g., a crisscross pattern), including in the expansion regions 106, for expansion and compression of the annuloplasty ring to allow transformation from a straight configuration in a delivery system to the operative geometry (e.g., D-shaped or C-shaped) at a delivery site within a heart. The expansion regions 106 may also allow the internal body member 100 to expand when within the heart so that the anchors 104 may be deployed into the heart valve annulus. After anchor deployment in such embodiments, the internal body member 100 is allowed to contract, which reduces the circumference of the heart valve annulus and reduces regurgitation. The internal body member 100 is configured to enable percutaneous, transcatheter annuloplasty to repair a heart valve. The internal body member 100 may be fastened, percutaneously, to the annulus of the heart valve while in the expanded state and then reduced to the contracted state to decrease an A-P distance of the target valve and thereby improve leaflet coaptation of the target valve and reduce regurgitation through the target valve.

In FIGS. 1A and 1B, as well as in other embodiments disclosed herein, the internal body member 100 may be arranged in a "D-shape" in the operable geometry (e.g., when implanted around the annulus). The D-shaped body member 100 has a certain geometrical ratio that is in conformance with the anatomical geometry of the annulus of the human mitral or tricuspid valve. For example, in certain embodiments the ratio of the A-P distance to the commissure-commissure (C-C) distance of the internal body member 100 when implanted (i.e., in the contracted state) is in a range between about 0.60 and about 0.70. In one embodiment, the implanted ratio of the A-P distance to the C-C distance is about 0.62.

In addition to the operable geometry, the internal body member 100 may be placed in an elongate insertion geometry such that the internal body member 100 can be inserted through a catheter into the heart. As discussed in detail below, in certain embodiments, the hypotube 102 may comprise a shape memory (e.g., Nitinol) hypotube into which a particular pattern is laser cut to form the device features, such as the expansion region 106 and/or anchors 104. The shape memory hypotube 102 is heat set to a "memorized" annular shape (e.g., the D-shaped operable geometry). The shape memory hypotube 102 is superelastic such that applying sufficient stress places the internal body member 100 into the elongate insertion geometry and releasing the stress allows the internal body member 100 to resume the D-shaped operable geometry. Although the illustrated embodiment of an internal body member 100 of FIG. 1A has a D-shaped operable geometry, artisans will recognize from the disclosure herein that other annular-shaped operable geometries may also be used. For example, circular, oval, or C-shaped operable geometries may be used.

Figure 1C:
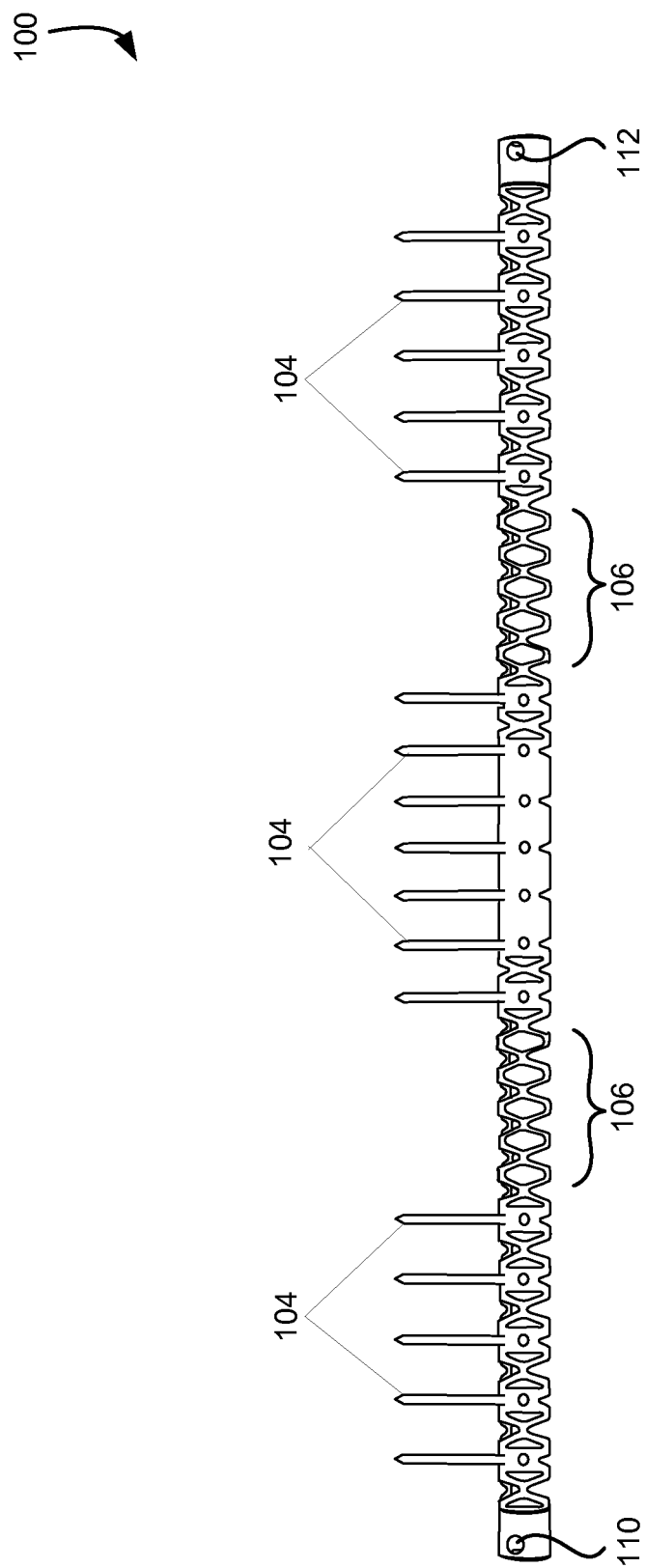
FIG. 1C is a side view of the internal body member shown in FIG. 1A in an elongated geometry.

The plurality of anchors 104 are configured to secure the internal body member 100 to the annulus of the heart valve. In certain embodiments, the anchors 104 are sufficient such that additional suturing of the annuloplasty ring to the valve annulus is not needed. In FIGS. 1A, 1B, and 1C, the anchors 104 are curved in the illustrated deployed configuration. The anchors 104 may be cut from the side of hypotube 102. When the anchors are first cut, they lie in the radial plane of the shape memory hypotube 102 and are concentric with the hypotube 102. The anchors 104 are then heat-set to the curved, deployed configuration. As shown in FIG. 1B, the heat-set anchors curve away from the hypotube 102. The heat-set anchors 104 may curve in the opposite direction from the curvature of the hypotube 102. For example, if newly cut anchors curve to the right, heat-set anchors would curve to the left. Although FIGS. 1A, 1B, and 1C show curved anchors 104, anchors in other embodiments may include other shapes, such as linear or helical deployed configurations. In certain embodiments, the anchors 104 include a shape memory material (e.g., Nitinol) that is heat set to a deployed configuration (e.g., linear, helical, or curved configuration shown in FIG. 1B). Artisans will recognize from the disclosure herein that combinations of barb designs and/or deployed configurations may also be used.

In some embodiments, the anchors 104 are superelastic such that applying sufficient stress places the anchors 104 into an introduction configuration and releasing the stress allows the anchors 104 to resume their respective deployed configurations. In certain embodiments, the anchors 104 lay in-line with the curvature of the internal body member 100 when in the introduction configuration to facilitate insertion of the internal body member 100 through the catheter. In such embodiments, the anchors 104 may be selectively deployed at a desired time (e.g., after the internal body member 100 is properly positioned against the annulus of the heart valve). The superelastic property of the anchors 104, combined with the opposite-curvature of the anchors in the introduction and deployed configurations, is used to self-propel the anchors 104 into the annulus of the heart valve. The opposite curvature of the anchors in the introduction and deployed configurations causes the anchors 104 to spring into tissue with extra force. In addition, or in other embodiments, an operator (e.g., a surgeon) applies a mechanical force to the internal body member 100 to propel the anchors 104 into the annulus of the heart valve.

The hypotube 102 includes one or more through holes 110, 112 at each end to allow one or more pins (not shown) to couple the male and female components of a device closure to respective ends of the hypotube 102. The hypotube 102 may also include a control window that allows one or more lines or sutures to exit the hypotube 102. The lines or sutures are used to snap lock the internal body member 100 into a ring shape and/or to deploy the anchors 104.

In FIG. 1C, the internal body member 100 is shown in the elongate insertion geometry. It should be noted, however, that the anchors 104 in FIG. 1C are shown in the extended (deployed) position, and not in a configuration suitable for insertion through a catheter. As discussed below, the internal body member 100 is formed from a straight (elongate) hypotube into which features, such as anchors 104, may be formed.

In addition to the operable geometry shown in FIGS. 1A and 1B the internal body member 100 is capable of making the transition from an elongate insertion geometry (FIG. 1C) to the annular operable geometry (FIGS. 1A and 1B). The elongate insertion geometry allows the internal body member 100 to be inserted into and passed through a catheter for percutaneous passage of the annuloplasty ring 600 into the heart of a patient. A transition from an elongate insertion geometry to an annular operable geometry is illustrated in FIGS. 16A, 16B, 16C, and 16D, and discussed below with reference to the same.

Although not shown in FIGS. 1A, 1B, and 1C, certain ring embodiments may include a selectively adjustable member for changing the size and/or shape of the internal body member 100 postoperatively to compensate for changes in the size of the heart and/or the treated heart valve. Examples of a selectively adjustable member are provided in U.S. patent application Ser. No. 13/198,582, filed Aug. 4, 2011, and titled PERCUTANEOUS TRANSCATHETER REPAIR OF HEART VALVES, which is hereby incorporated by reference herein in its entirety.

Figure 2:
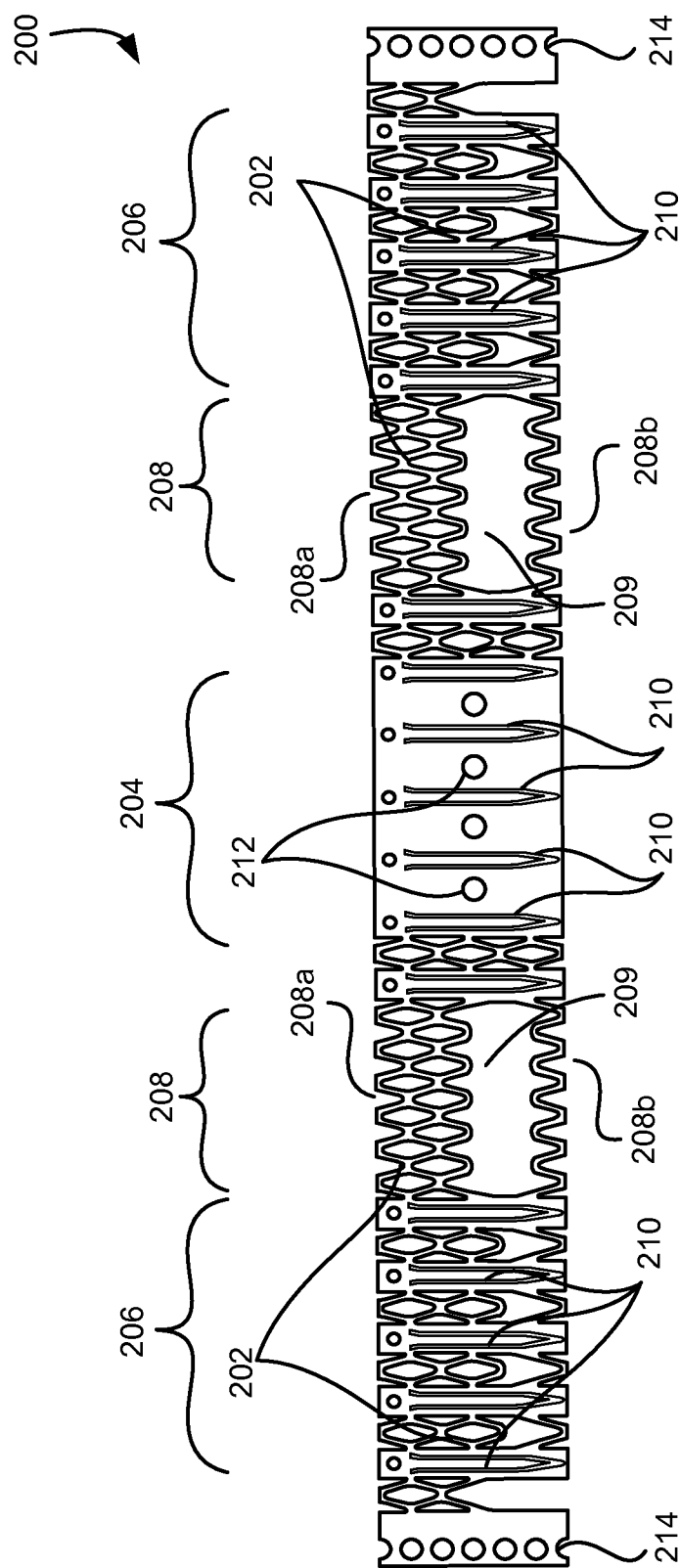
FIG. 2 is a schematic diagram of a cutting pattern used to form the internal body member shown in FIG. 1A according to certain embodiments.

FIG. 2 is a schematic diagram of a cutting pattern 200 used for laser processing hypotubes, such as the hypotube 102 shown in FIGS. 1A, 1B, and 1C. The cutting pattern 200 corresponds to the entire hypotube 102 as if the hypotube 102 were cut along a longitudinal axis and unrolled. Thus, for example, each expansion region 106 shown in FIG. 1C is shown in FIG. 2 as being split between a first half of the expansion region 208a and a second half of the expansion region 208b.

The cutting pattern 200 defines the configuration of a hypotube (e.g., hypotube 102) and defines how regions of the hypotube (e.g., expansion regions 106) interact with adjacent regions as the hypotube transitions from an elongate insertion geometry (see e.g., FIG. 1C) to an annular operable geometry (see e.g., FIGS. 1A and 1B). As shown in FIG. 2, the cutting pattern 200 in this example embodiment includes a "crisscross" pattern 202. The crisscross pattern 202 allows for increased expansion and/or contraction in regions of the hypotube containing the crisscross pattern 202. One or more rigid regions 204, semi-rigid regions 206, and expansion regions 208 may be defined using the crisscross pattern 202. The rigid region 204 does not include the crisscross pattern 202. The semi-rigid region 206 includes an intermittent crisscross pattern 202. The crisscross pattern 202 is throughout the expansion region 208. The expansion region 208 may also include large gaps or cutout regions 209 to allow increased flexibility or bending of the internal body member (e.g., at the corners of the D-shape as shown in FIG. 1B at the expansion regions 106). The cutting pattern 200 also includes anchor cutouts 210, control window cutouts 212, and through hole cutouts 214. The anchor cutouts 210 define the length, width, and location of annuloplasty ring anchors, such as anchors 104. Similarly, the control window cutouts 212 and through hole cutouts 214 define the size, geometry, and location of control windows and through holes in the hypotube. The cutting pattern 200 defines the annular operable geometry of a hypotube, allows the hypotube to easily transition from the elongate insertion geometry to the annular operable geometry, and allows for adjustment in the anterior-posterior (A-P) dimension to ensure that the annulus is sufficiently reduced.

Figure 3:
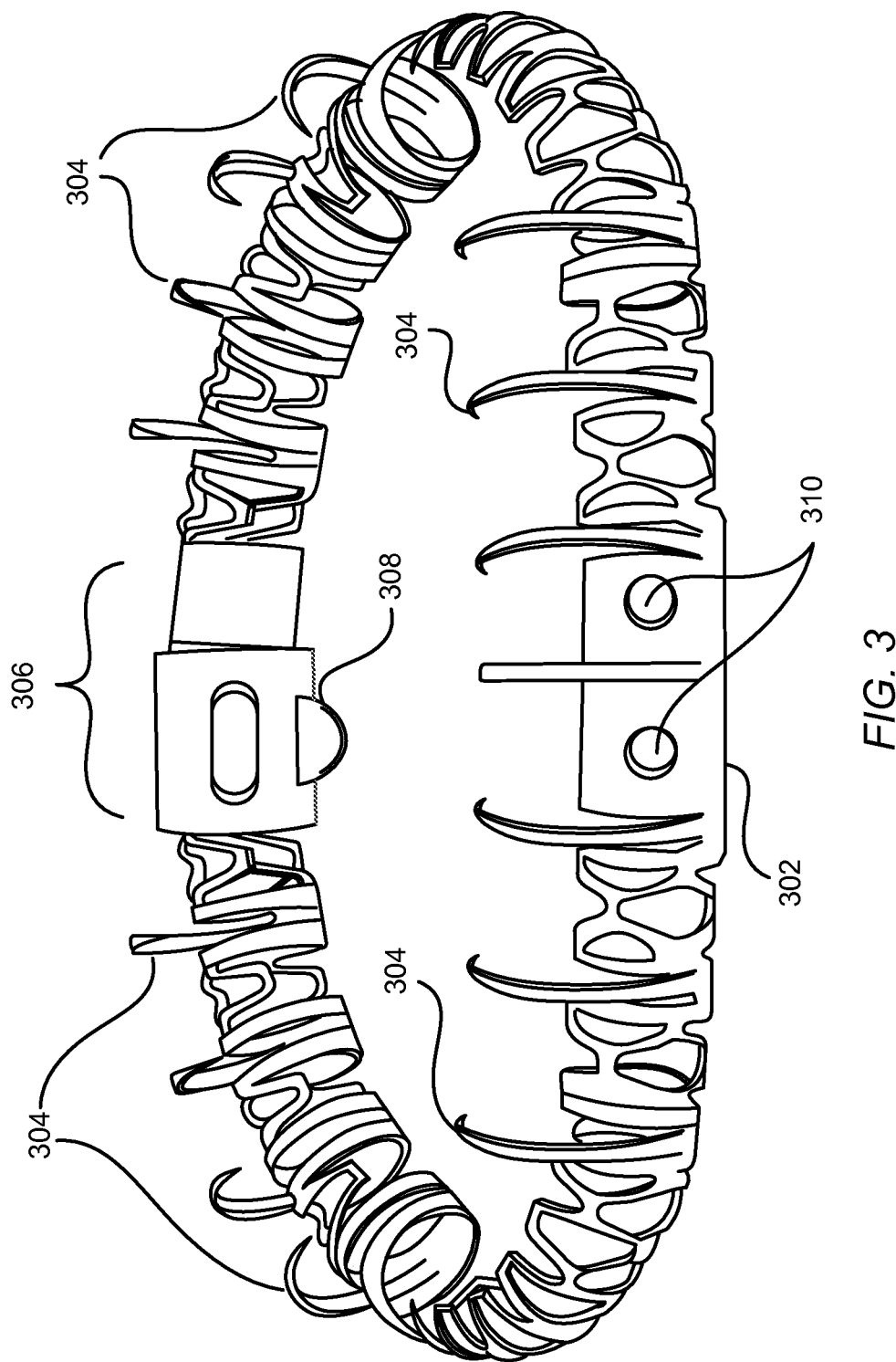
FIG. 3 is a perspective view of a body member and a device closure of an annuloplasty ring according to certain embodiments.

FIG. 3 is a perspective view of a body member 302 and a device closure 306 of an annuloplasty ring for percutaneous, trans-catheter annuloplasty repair according to certain embodiments. The illustrated body member 302 may be similar to the internal body member 100 discussed above in reference to FIGS. 1A, 1B, and 1C.

The body member 302 is laser cut into a desired shape. A cutting pattern, such as cutting patter 200 shown in FIG. 2, may be used to define regions of the body member 302 where the body member 302 may be flexible or rigid. In certain embodiments, anchors 304 are cut from the body member 302. In other embodiment, the anchors 304 may be attached to body member 302 by welding, adhesive, or other suitable fastening means. The anchors 304 are configured to attach the annuloplasty ring to the heart valve annulus.

The device closure 306 is used to secure two open ends of the annuloplasty ring to form a closed ring of the operable geometry. In certain embodiments, a ring closure lock includes a female snap and a male snap. Examples of ring closure locks are provided in U.S. patent application Ser. No. 13/779,478.

A pivot 308 is attached to body member 302 and/or the device closure 306 and is used to rotate the annuloplasty ring after deployment via catheter within the heart to align the plane of the annuloplasty ring (in the annular operable geometry) with the plane of the heart valve. The pivot 308 may be manually coupled (e.g., using a pin, etc.), welded, or bonded using an adhesive. Upon exiting the catheter, the annuloplasty ring may be rotated via the pivot 308 to allow the annuloplasty ring to be properly positioned against the heart valve annulus. In some embodiments, the pivot 308 is used to rotate the annuloplasty ring such that the anchors 304 are propelled into the surrounding annular tissue.

FIGS. 4A, 4B, 4C, 4D, 4E, and 4F are perspective views of an anchor deployment system 400 for deploying anchors of an annuloplasty ring into a heart valve annulus. The system 400 includes a body member 402 with a plurality of anchors 404, a plurality of retainer features 406, and a retaining ribbon 408. The body member 402 also includes the body members 100, 300 discussed above in reference to FIGS. 1A, 1B, and 1C and FIG. 3. The anchors 404 are heat treated to extend away from the body member 402 so as to anchor the body member 402 into heart valve annulus tissue. In some embodiments, the anchors 404 curve away from the body member 402. The anchors 404 may curve in the opposite direction from the body member 402. For example, if newly cut anchors curve to the right, heat-set anchors would curve to the left, similar to the anchors 104 shown in FIG. 1B.

Referring again to FIGS. 4A, 4B, 4C, 4D, 4E, and 4F, certain annuloplasty ring embodiments include the retaining ribbon 408 disposed about an outer circumference of the body member 402, or selected portions thereof. The retaining ribbon 408 prevents the anchors 404 from deploying until the annuloplasty ring is properly positioned against the heart valve annulus. The retainer features 406 are disposed in pairs on either side of each anchor 404 and are configured to hold the retaining ribbon 408 against the surface body member 402. The plurality of anchors 404 have superelastic properties allowing them to spring back into their heat-set shape as described above. Additionally, the opposite-curvature of the anchors causes the anchors 404 to spring into tissue with extra force. Prior to deployment, stress is applied to anchors 404 causing them to lie flush with the body member 402. The retaining ribbon 408 is inserted between the anchors 404 and the retainer features 406 thereby holding the anchors 404 flush with the body member 402. In some embodiments, when the body member 402 is configured in the operable geometry and positioned around the annulus, the retaining ribbon 408 is retracted so that the anchors 404 deploy. When the retaining ribbon 408 retracts past an anchor 404, the stress on the anchor 404 is released causing the anchor 404 to self-deploy into the annulus tissue. In other embodiments, the anchors 404 are deployed before the body member 402 is placed in the operable geometry.

Figure 4A:
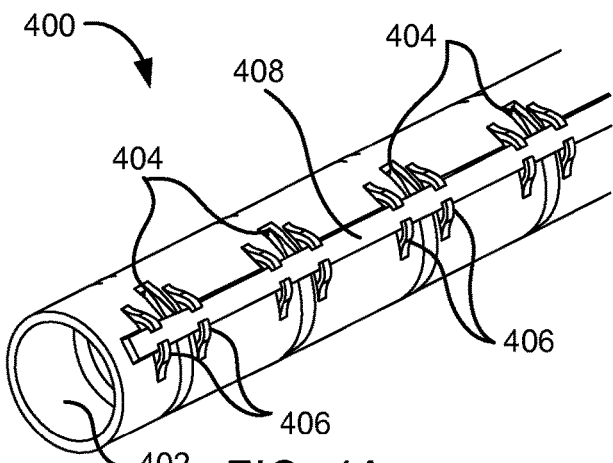
FIG. 4A is a perspective view of an anchor deployment system according to certain embodiments.
Figure 4B:
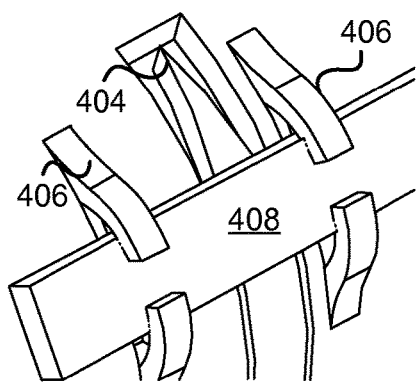
FIG. 4B is an enlarged view of the anchor deployment system shown in FIG. 4A.

FIGS. 4A and 4B are views of an anchor deployment system 400 wherein the retaining ribbon 408 is disposed between the anchors 404 and the retainer features 406. FIG. 4B is an enlarged view of the anchor deployment system of FIG. 4A showing how the retaining ribbon 408 is disposed between an anchor 404 and a pair of retainer features 406 thereby preventing the anchor 404 from deploying.

Figure 4C:
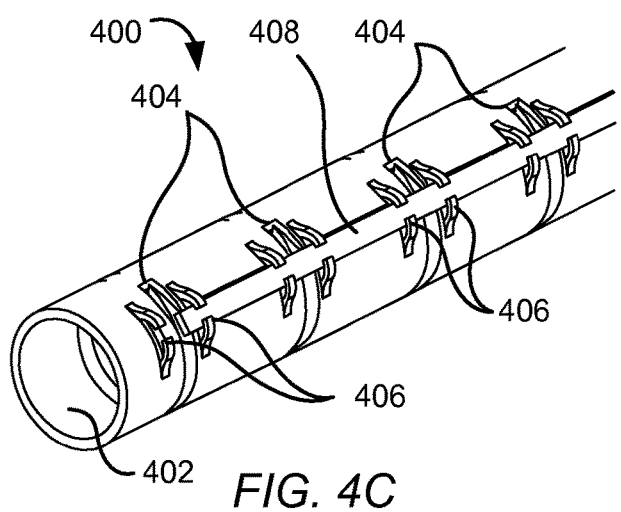
FIG. 4C is a perspective view of the anchor deployment system shown in FIG. 4A in a partially retracted state.
Figure 4D:
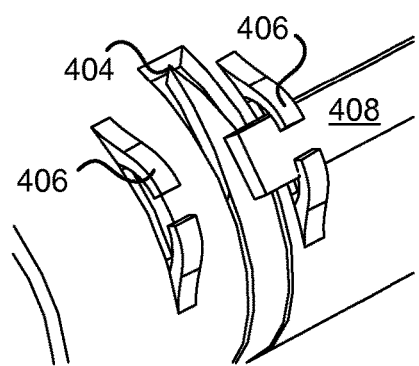
FIG. 4D is an enlarged view of the anchor deployment system shown in FIG. 4C.

FIGS. 4C and 4D are views of the anchor deployment system 400 when the retaining ribbon 408 is partially retracted past an anchor 404. In some embodiments, the strength and/or rigidity of the retaining ribbon 408 is sufficient to prevent the anchor 404 from deploying until the retaining ribbon 408 has retracted across the entire anchor 404. In other embodiments, the strength and/or rigidity of the retaining ribbon 408 is sufficient to prevent the anchor 404 from deploying until the retaining ribbon 408 has retracted halfway across the anchor 404. In yet other embodiments, the strength and/or rigidity of the retaining ribbon 408 is only sufficient to prevent the anchor 404 from deploying until the retaining ribbon 408 has retracted past the first retainer feature 406 of the pair of retainer features 406 surrounding the anchor 404. FIG. 4D is an enlarged view of the anchor deployment system of FIG. 4C showing how the retaining ribbon is partially retracted across an anchor 404.

Figure 4E:
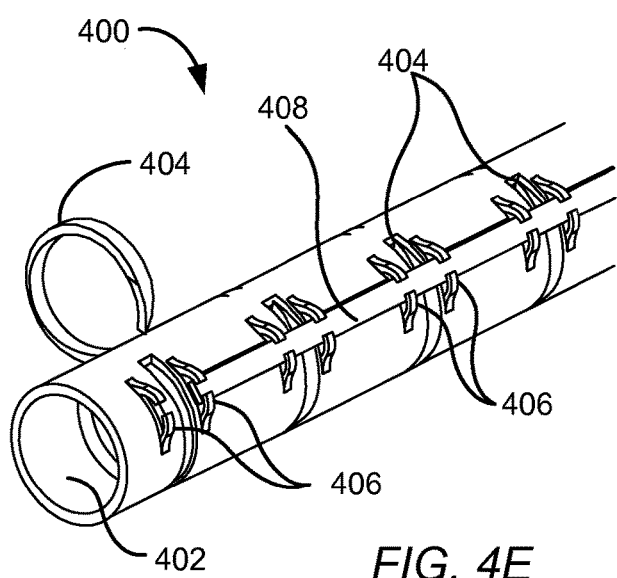
FIG. 4E is a perspective view of the anchor deployment system shown in FIG. 4A in a retracted state.
Figure 4F:
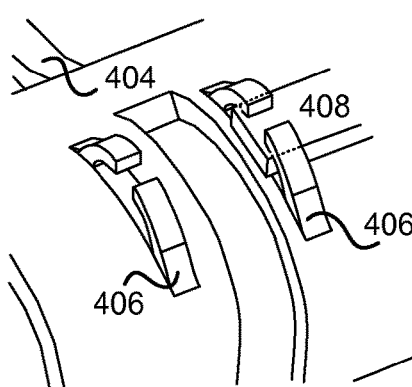
FIG. 4F is an enlarged view of the anchor deployment system shown in FIG. 4E.

FIGS. 4E and 4F are views of the anchor deployment system 400 when the retaining ribbon 408 is fully retracted past an anchor 404. When the force applied to an anchor 404 by the retaining ribbon 408 becomes insufficient, the anchor 404 self-propels into the annulus tissue thereby anchoring the annuloplasty ring into the heart valve annulus. FIG. 4F is an enlarged view of the anchor deployment system of FIG. 4E showing the retaining ribbon fully retracted past an anchor 404.

FIGS. 5A, 5B, 5C, and 5D are perspective views of an anchor deployment system 500 for deploying anchors of an annuloplasty ring into a heart valve annulus according to certain embodiments. The system 500 includes a body member 502 with a plurality of anchors 504, and an outer tube or retaining cover 506. In some embodiments, the retaining cover 506 includes a plurality of deployment windows 508 through which the plurality of anchors 504 are deployed, each deployment window 508 corresponding to an anchor 504. In yet other embodiments, the plurality of anchors 504 are configured to puncture through the retaining cover 506 during deployment. The body member 502 may be similar to the body member 100, 300, and 402 discussed above in reference to FIGS. 1A, 1B, and 1C, 3, and 4A, 4B, 4C, 4D, 4E, and 4F. The anchors 504 have been heat treated to extend away from the annuloplasty ring 502 so as to anchor the annuloplasty ring 502 into heart valve annulus tissue.

Certain annuloplasty ring embodiments include an outer tube or retaining cover 506 disposed about the entire circumference of the annuloplasty ring 502, or selected portions thereof. For example, in certain embodiments, the retaining cover 506 is disposed so as to enclose the anchors 504 and the expansion region(s), while leaving uncovered at least portions of a closure mechanism (to permit snapping the ends of the annuloplasty ring together). The retaining cover 506 prevents the anchors 504 from deploying until the annuloplasty ring is properly positioned against the heart valve annulus. The plurality of anchors 504 have superelastic properties allowing them to spring back into their heat-set shape as described above. The superelastic property of the anchors 504, combined with the opposite-curvature of the anchors, is used to self-propel the anchors 504 into the annulus of the heart valve. The opposite curvature of the anchors 504 causes them to spring into tissue with extra force. Prior to deployment, stress is applied to anchors 504 causing them to lie flush with the body member 502. The body member 502, including anchors 504, is inserted into the retaining cover 506 thereby holding the anchors 504 flush with the body member 502 and preventing their deployment. In some embodiments, when the annuloplasty ring is configured in the operable geometry and positioned around the annulus, the body member 502 is rotated within the retaining cover 506. When the anchors 504 are rotated to the deployment windows 508, the stress on the anchors 504 is released, allowing the anchors 504 to self-deploy into the annulus tissue. In other embodiments, the anchors 504 are deployed before the annuloplasty ring 502 is placed in the operable geometry.

FIG. 5A is a perspective view of the retaining cover 506 including the plurality of deployment windows 508. The retaining cover 506 may include a biocompatible material such as Dacron®, woven velour, polyurethane, polytetrafluoroethylene (PTFE), heparin-coated fabric, or the like. In other embodiments, the retaining cover 506 includes a biological material such as bovine or equine pericardium, homograft, patient graft, or cell-seeded tissue.

FIG. 5B is a perspective view of the body member 502 after being inserted into the retaining cover 506. In FIG. 5B, the body member 502 is in the elongated configuration. After being deployed into the heart through a catheter, the body member 502 is placed into an annular operable geometry. The retaining cover 506 is flexible and continues to surround the annuloplasty ring 502 while in the operable geometry.

FIG. 5C is an enlarged perspective view of the anchor deployment system 500. As seen in FIG. 5C, the tip 504a of the anchor 504 is at the deployment window 508, but the body member 502 may be rotated further before the anchor 504 deploys into the annular tissue. As the body member 502 rotates in the direction of arrow 510, the elastic force of the anchor 504 causes the tip 504A to protrude from the deployment window 508. Further rotation in the direction of the arrow 510 causes more of the anchor 504 to protrude beyond the retaining cover 506 as the anchor deploys.

FIG. 5D is an enlarged perspective view of the anchor deployment system 500. As seen in FIG. 5D, the continued rotation of the body member 502 causes the anchor 504 to deploy. Referring back to FIGS. 5A and 5B, in the illustrated embodiment, the deployment windows 508 are aligned with each other causing all the anchors 504 to simultaneously deploy as the body member 502 rotates within the retaining cover 506. In other embodiments, the deployment windows 508 may be disposed on the retaining cover 506 in an unaligned manner so that the anchors 504 deploy in a desired sequence. Where simultaneous deployment is not desired, the deployment windows 508 may have oval, oblong, or rectangular shapes so that continued rotation will not retract deployed anchors or displace the annuloplasty ring 502 from its position around the heart valve annulus.

Figure 6:
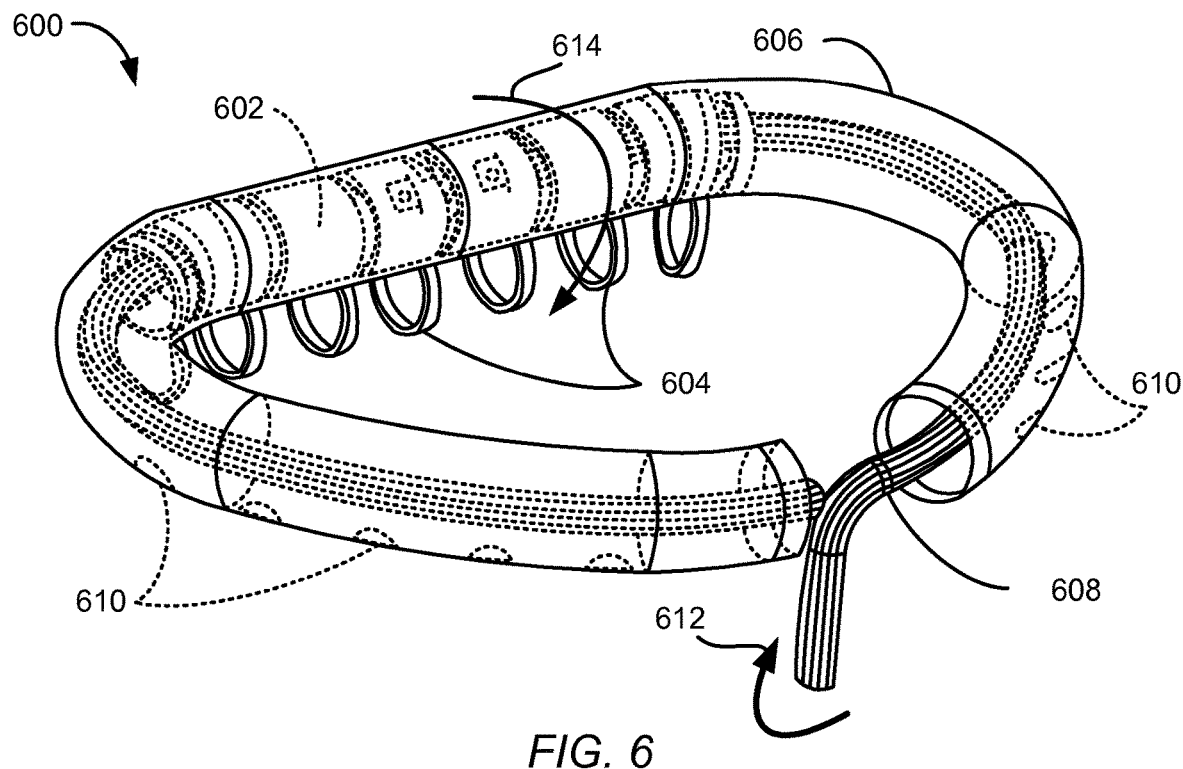
FIG. 6 is a perspective view of an annuloplasty ring including an anchor deployment system according to certain embodiments.

FIG. 6 is a perspective view of an annuloplasty ring 600 including an anchor deployment system according to certain embodiments. In some embodiments, the anchor system shown in FIG. 6 may be combined with the anchor deployment system 500 shown in FIG. 5. The annuloplasty ring 600 includes a shape memory body member 602, a plurality of anchors 604, an outer tube 606, and a deployment wire 608. The deployment wire 608 is attached to the body member 602 and is used to selectively deploy the anchors 604. The plurality of anchors 604 are attached to the shape memory body member 602. In some embodiments, the anchors 604 are welded to the shape memory body member 602. In other embodiments, the anchors 604 are laser cut from the side of the shape memory body member 602 and then heat-set to a curved, deployed configuration, similar to the anchors 104 discussed above in reference to FIGS. 1A, 1B, and 1C. In some embodiments, the anchors 604 are curved when in the deployed configuration. The anchors 604 may curve away from the body member 602. In some embodiments, the anchors 604 curve in the opposite direction from the body member 602. The anchors 604 in other embodiments may include other shapes, such as linear or helical deployed configurations. In certain embodiments, the anchors 604 include a shape memory material (e.g., Nitinol) that is heat set to a deployed configuration (e.g., linear, helical, or curved). Artisans will recognize from the disclosure herein that combinations of barb designs and/or deployed configurations may also be used.

In some embodiments, the anchors 604 are superelastic such that applying sufficient stress places the anchors 604 into an introduction configuration and releasing the stress allows the anchors 604 to resume their respective deployed configurations. In certain embodiments, the anchors 604 lay in-line with the body member 602 when in the introduction configuration to facilitate insertion of the annuloplasty ring 600 through a catheter. The body member 602, including the anchors 604, is inserted into the outer tube 606 thereby holding the anchors 604 flush with the body member 602 and preventing their deployment. In some embodiments, the body member 602 runs the full length of the outer tube 606. In other embodiments, the body member 602 is segmented into multiple segments. The outer tube 606 prevents the anchors 604 from deploying until properly positioned against the heart valve annulus. In such embodiments, the anchors 604 may be selectively deployed at a desired time (e.g., after the body member 602 is properly positioned against the annulus of the heart valve). The superelastic property of the anchors 604, combined with the opposite curvature of the anchors, causes the anchors 604 to spring into tissue with extra force.

When the annuloplasty ring 600 is configured in an operable geometry and positioned around the annulus, the body member 602 is rotated within the outer tube 606 via the deployment wire 608, causing the anchors 604 to deploy. The deployment wire 608 passes inside the outer tube 606 and attaches to the body member 602. The deployment wire 608 is a torque wire capable of applying torque to the body member 602. To deploy the anchors, the deployment wire 608 is rotated in the direction of arrow 612, which results in the body member 602 rotating in the direction of arrow 614. As the body member 602 rotates, the anchors 604 deploy through the outer tube 606.

In some embodiments, the outer tube 606 includes a plurality of anchor deployment windows 610 that allow the anchors 604 to pass through the outer tube 606. When the anchors 604 are rotated within the outer tube 606 to the deployment windows 610, the stress on the anchors 604 is released allowing the anchors 604 to deploy. The superelastic property of the anchors 604, combined with the opposite curvature of the anchors, causes the anchors 604 to vigorously spring out of the deployment windows 610.

The outer tube 606 may include a biocompatible material such as Dacron®, woven velour, polyurethane, polytetrafluoroethylene (PTFE), heparin-coated fabric, or the like. In other embodiments, the outer tube 606 includes a biological material such as bovine or equine pericardium, homograft, patient graft, or cell-seeded tissue.

Figure 7A:
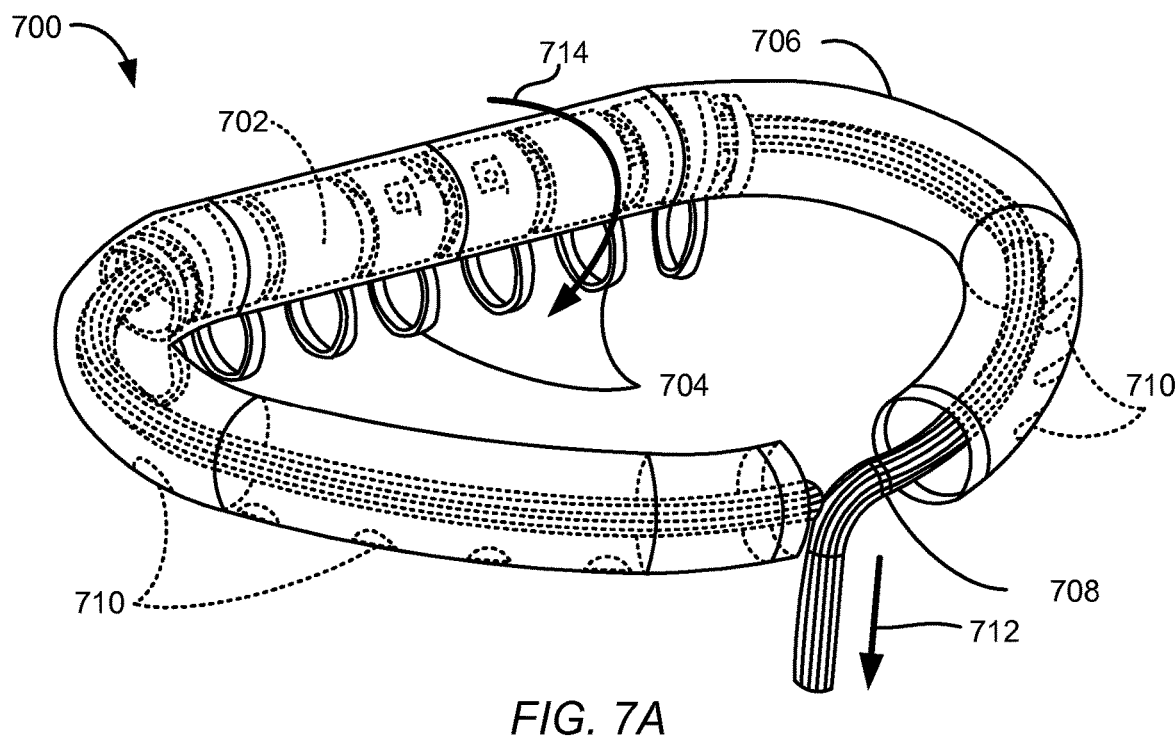
FIG. 7A is a perspective view of annuloplasty ring including another anchor deployment system according to certain embodiments.

FIG. 7A is a perspective view of an annuloplasty ring 700 including another anchor deployment system according to the present disclosure. In some embodiments, the anchor system shown in FIG. 7 may be combined with the anchor deployment system 500 shown in FIG. 5. The anchor deployment system is used to deploy anchors of an annuloplasty ring 700, such as those described in the present disclosure. The annuloplasty ring 700 includes a shape memory body member 702, a plurality of anchors 704, an outer tube 706, and a deployment wire 708. The deployment wire 708 is attached to the body member 702 and is used to selectively deploy the anchors 704. The plurality of anchors 704 are attached to the shape memory body member 702. In some embodiments, the anchors 704 are welded to the shape memory body member 702. In other embodiments, the anchors 704 are laser cut from the side of the shape memory body member 702 and then heat-set to a curved, deployed configuration, similar to the anchors 104 discussed above in reference to FIGS. 1A, 1B, and 1C. In some embodiments, the anchors 704 are curved when in the deployed configuration. The anchors 704 may curve away from the body member 702. In some embodiments, the anchors 704 curve in the opposite direction from the body member 702. The anchors 704 in other embodiments may include other shapes, such as linear or helical deployed configurations. In certain embodiments, the anchors 704 include a shape memory material (e.g., Nitinol) that is heat set to a deployed configuration (e.g., linear, helical, or curved). Artisans will recognize from the disclosure herein that combinations of barb designs and/or deployed configurations may also be used.

In some embodiments, the anchors 704 are superelastic such that applying sufficient stress places the anchors 704 into an introduction configuration and releasing the stress allows the anchors 704 to resume their respective deployed configurations. In certain embodiments, the anchors 704 lay in-line with the body member 702 when in the introduction configuration to facilitate insertion of the body member 702 through the catheter. The body member 702, including anchors 704, is inserted into the outer tube 706 thereby holding the anchors 704 flush with the body member 702 and preventing their deployment. In some embodiments, the body member 702 runs the full length of the outer tube 706. In other embodiments, the body member 702 is segmented into multiple segments. The outer tube 706 prevents the anchors 704 from deploying until properly positioned against the heart valve annulus. In such embodiments, the anchors 704 may be selectively deployed at a desired time (e.g., after the annuloplasty ring is properly positioned against the annulus of the heart valve). The superelastic property of the anchors 704, combined with the opposite curvature of the anchors, causes the anchors 704 to spring into tissue with extra force.

When the annuloplasty ring 700 is configured in an operable geometry and positioned around the annulus, the body member 702 is rotated within the outer tube 706 via the deployment wire 708, causing the anchors 704 to deploy. The deployment wire 708 passes inside the outer tube 706 and is coupled to a rotation member (not shown). The rotation member transforms linear movement of the deployment wire 708 into rotational movement of the body member 702. To deploy the anchors 704, the deployment wire 708 is pulled in the direction of arrow 712, which results in the body member 702 rotating in the direction of arrow 714. As the body member 702 rotates, the anchors 704 deploy through the outer tube 706.

In some embodiments, the outer tube 706 includes a plurality of anchor deployment windows 710 that allow the anchors 704 to pass through the outer tube 706. When the anchors 704 are rotated within the outer tube 706 to the deployment windows 710, the stress on the anchors 704 is released allowing the anchors 704 to deploy. The superelastic property of the anchors 704, combined with the opposite curvature of the anchors, causes the anchors 704 to vigorously spring out of the deployment windows 710.

The outer tube 706 may include a biocompatible material such as Dacron®, woven velour, polyurethane, polytetrafluoroethylene (PTFE), heparin-coated fabric, or the like. In other embodiments, the outer tube 706 includes a biological material such as bovine or equine pericardium, homograft, patient graft, or cell-seeded tissue.

Figure 7C:
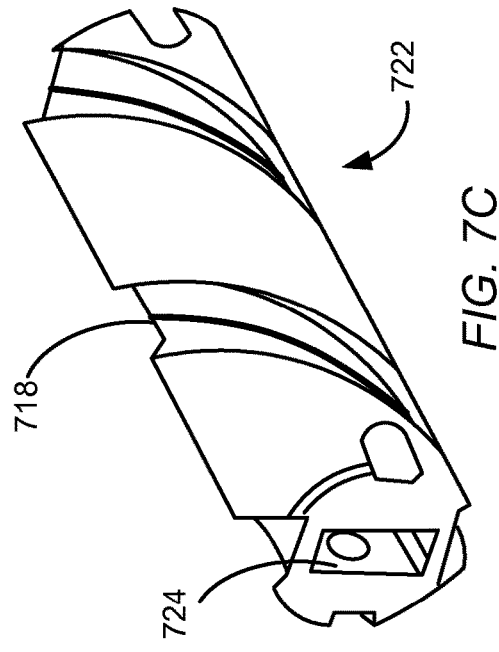
FIG. 7C is a perspective view of another rotation member for use in the anchor deployment system shown in FIG. 7A according to certain embodiments.
Figure 7E:
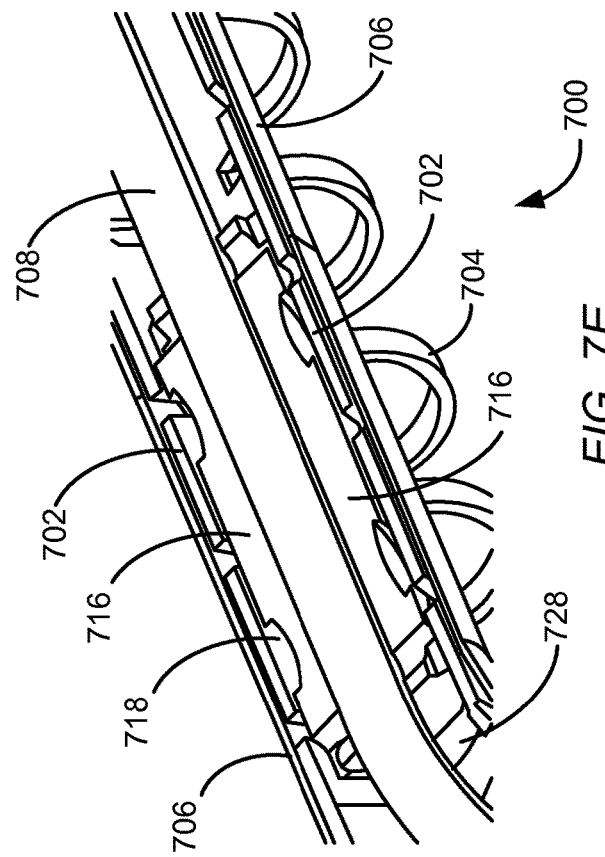
FIG. 7E is a cross-sectional, perspective view of the annuloplasty ring including the anchor deployment system shown in FIG. 7A.
Figure 7B:
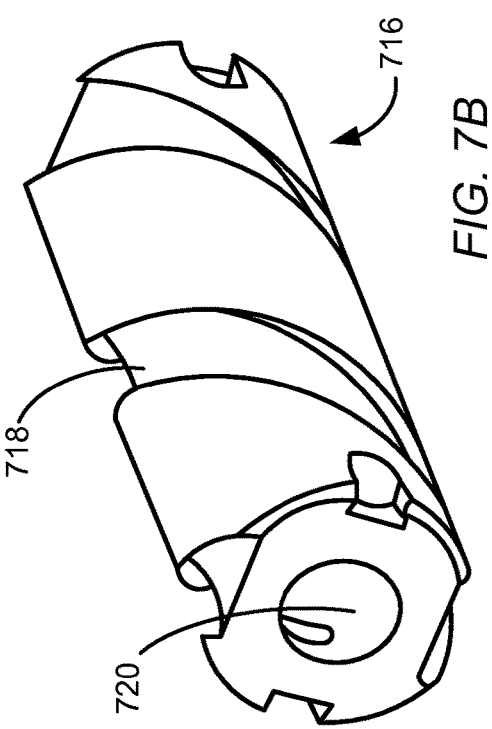
FIG. 7B is a perspective view of a rotation member for use in the anchor deployment system shown in FIG. 7A according to certain embodiments.

FIG. 7B is a perspective view of a rotation member 716 for use with the anchor deployment system 700 shown in FIG. 7A according to certain embodiments. The rotation member 716 includes one or more threaded grooves 718 configured to apply torque to the body member 702. The rotation member 716 further includes a hole 720 through which a round wire (such as deployment wire 708) may pass.

FIG. 7C is a perspective view of a rotation member 722 for use with the anchor deployment system 700 shown in FIG. 7A according to certain embodiments. The rotation member 722 includes one or more threaded grooves 718 configured to apply torque to the body member 702. The rotation member 722 further includes a hole 724 through which a flat wire or ribbon (such as deployment wire 708) may pass.

Figure 7D:
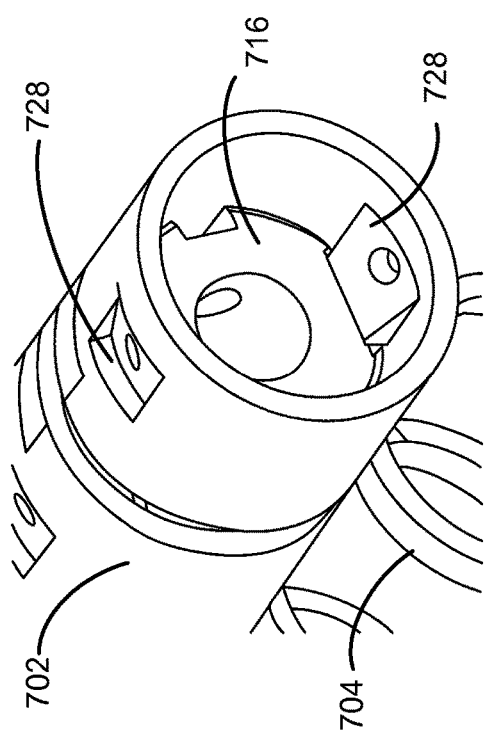
FIG. 7D is an enlarged perspective view of the annuloplasty ring including the anchor deployment system shown in FIG. 7A.

FIG. 7D is an enlarged perspective view of the annuloplasty ring including the anchor deployment system shown in FIG. 7A. In some embodiments, the body member 702 includes one or more inner tabs 728 configured to engage the threaded grooves 718 of the rotation member 716 shown in FIG. 7B (or the rotation member 722 shown in FIG. 7C). As the deployment wire 708 moves linearly (e.g., is pushed or pulled by a user), the rotation member 716 applies torque to the body member 702 via the groove 718 moving along the inner tabs 728. The rotation of body member 702 causes anchors 704 to deploy.

FIG. 7E is a cross-sectional, perspective view of the annuloplasty ring including the anchor deployment system shown in FIG. 7A. As shown, the deployment wire 708 passed through rotation member 716. Rotation member 716 is located inside body member 702 and the threaded grooves 718 engage the inner tabs 728 to cause body member 702 to rotate within outer tube 706. When the rotation of body member 702 causes the anchors 704 to reach the deployment windows 710, the anchors 704 deploy through the outer tube 706.

Example Ring Embodiments with Separately Deployed Anchors

Figure 8A:
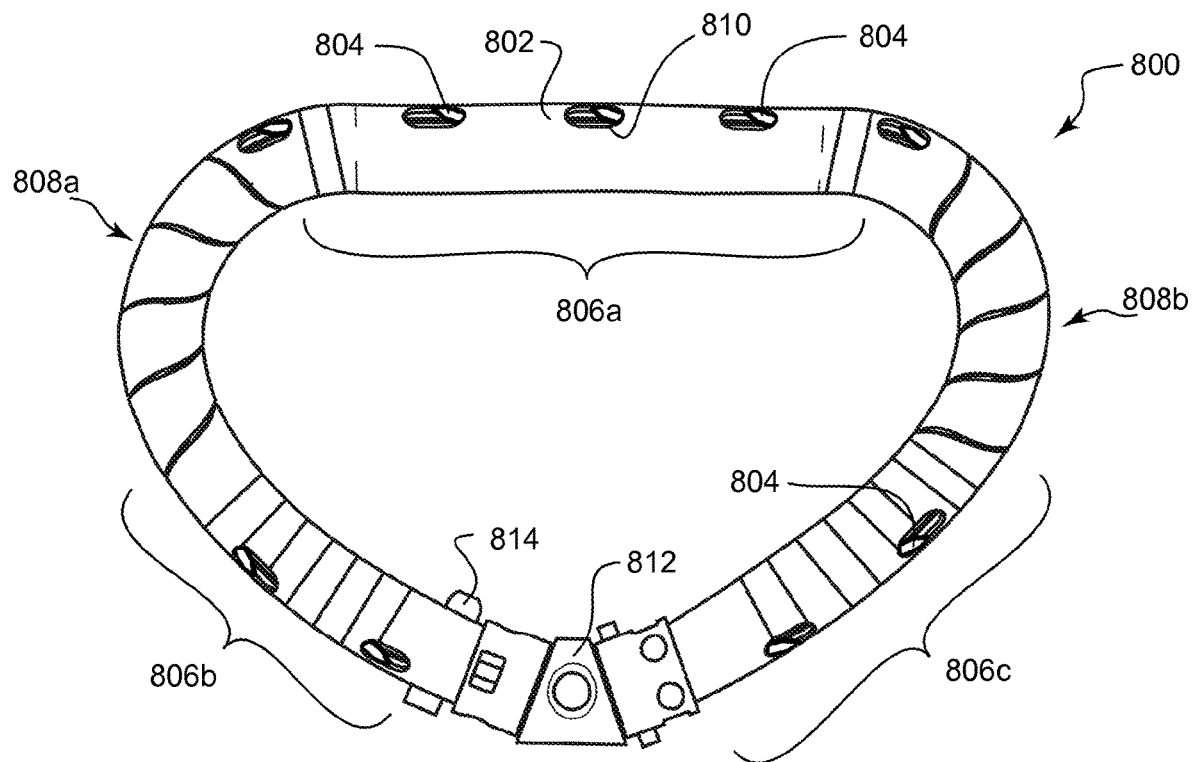
FIG. 8A is top view of an annuloplasty ring in an operative geometry according to certain embodiments.

FIG. 8A is top view of an annuloplasty ring 800 in an operative geometry according to certain embodiments. The annuloplasty ring 800 illustrated in FIG. 8A is in an annular (D-shaped) operable geometry in a contracted state. The annuloplasty ring 800 is configured to enable percutaneous, transcatheter annuloplasty repair of a heart valve. The annuloplasty ring 800 may be fastened, percutaneously, to the annulus of the heart valve while in the expanded state and then reduced to the contracted state to decrease an A-P distance of the target valve and thereby improve leaflet coaptation of the target valve and reduce regurgitation through the target valve.

The annuloplasty ring 800 includes a body member 802 having a plurality of anchors 804, a plurality of anchor regions 806a, 806b, 806c (collectively 806), a plurality of expansion regions 808a, 808b (collectively 808), a plurality of anchor windows 810, a ring closure lock 812, and a pivot 814. In some embodiments, the anchors 804 may be separately deployed through the anchor windows 810. In FIG. 8A the body member 802, including the plurality of regions 806, 808, is arranged in a "D-shape" in the operable geometry. The D-shaped annuloplasty ring 800 has a certain geometrical ratio that is in conformance (or approximate conformance) with the anatomical geometry of the human mitral valve annulus. For example, in certain embodiments the ratio of the A-P distance to the commissure-commissure (C-C) distance of the annuloplasty ring 800 when implanted (i.e., in the contracted state) is in a range between about 0.60 and about 0.70. In one embodiment, the implanted ratio of the A-P distance to the C-C distance is about 0.62.

Although the illustrated embodiment of an annuloplasty ring 800 of FIG. 8A is a D-shaped operable geometry, artisans will recognize from the disclosure herein that other annular-shaped operable geometries may also be used. For example, circular, oval, or C-shaped operable geometries may be used.

The body member 802 may be cut from, for example, a tube to form the plurality of regions 806, 808. The cuts may define a shape and/or characteristics of the body member 802. For example, the laser cuts may define the anchor regions 806, expansion regions 808, and/or the anchor windows 810. The laser cuts may also define how the plurality of regions 806, 808 interacts.

In certain embodiments, the body member 802 may include a shape memory (e.g., Nitinol) hypotube into which a plurality of cuts and/or segments may be laser cut to define a size, shape, and/or characteristics of the plurality of regions 806, 808. The shape memory body member 802 may be heat set to a "memorized" annular shape (e.g., the D-shaped operable geometry). The shape memory body member 802 may be superelastic such that applying sufficient stress may place the annuloplasty ring 800 into the elongate insertion geometry and releasing the stress allows the annuloplasty ring 800 to resume the D-shaped operable geometry.

In addition to the operable geometry shown in FIG. 8A the annuloplasty ring 800 is transitionable from an elongate insertion geometry to the annular operable geometry shown in FIG. 8A. The elongate insertion geometry allows the annuloplasty ring 800 to be inserted into and passed through a catheter for percutaneous passage of the annuloplasty ring 800 into the heart of a patient. A transition from an elongate insertion geometry to an annular operable geometry is illustrated in FIGS. 16A, 16B, 16C, and 16D, and discussed below with reference to the same.

The anchors 804 are configured to secure the annuloplasty ring 800 to the annulus of the heart valve. In certain embodiments, the anchors 804 are sufficient such that additional suturing of the annuloplasty ring 800 to the valve annulus is not needed. In FIG. 8A the anchors 804 are within the body member 802 in an introduction configuration. The anchors 804 may be later deployed, as discussed below with reference to FIGS. 9A, 9B, 9C, 9D, and 9E and FIGS. 10A, 10B, 10C, and 10D. The anchors 804 may be selected from a plurality of shapes, such as curved, linear, or helical deployed configurations. In certain embodiments, the anchors 804 include a shape memory material (e.g., Nitinol) that is heat set to a deployed configuration (e.g., curved configuration, linear configuration, or helical configuration). Artisans will recognize from the disclosure herein that combinations of different deployed anchor configurations may also be used.

In some embodiments, the anchors 804 are in the same plane as the annuloplasty ring. In other embodiments, the anchors 804 deploy at an angle to the plane of the annuloplasty ring, such as 10°, 45°, or even 90°.

In some embodiments, there are two or more anchor sections in the annuloplasty ring 800. The anchors 804 are integral to each anchor section. Each anchor section may include two or more anchors 804. Additionally, multiple anchor sections may be placed in parallel with each other to affect a more secure attachment of the ring to the native annulus.

The anchors 804 are superelastic such that applying sufficient stress places the anchors 804 into an introduction configuration and releasing the stress allows the anchors 804 to resume their respective deployed configurations. In certain embodiments, the anchors 804 are retracted inside the body member 802 of the annuloplasty ring 800 in the introduction configuration during insertion of the annuloplasty ring 800 through the catheter. In such embodiments, the anchors 804 may be selectively deployed at a desired time (e.g., after the annuloplasty ring 800 is properly positioned against, or in abutment with, the annulus of the heart valve). In certain embodiments, the superelastic property of the anchors 804 is used to self-propel the anchors 804 into the annulus of the heart valve. The superelastic property of the anchors 804, combined with the curvature of the anchors, causes the anchors 804 to spring into tissue with extra force. The anchors 804 may be configured to be deployed from within the body member 802 through anchor windows 810.

The ring closure lock 812 is used to secure two open ends of the annuloplasty ring 800 to form a closed ring of the operable geometry. In certain embodiments, the ring closure lock 812 includes a female snap and a male snap. Examples of ring closure locks are provided in U.S. patent application Ser. No. 13/779,478.

The pivot 814 is used to automatically rotate the annuloplasty ring 800 after it exits the catheter within the heart to align the plane of the annuloplasty ring 800 (in the annular operable geometry) with the plane of the heart valve. The annuloplasty ring 800 is pushed from the catheter in a direction that is substantially perpendicular to the plane of the heart valve (e.g., parallel to the general direction of blood flow through the valve). Upon exiting the catheter, the annuloplasty ring 800 is rotated at or about the pivot 814 to allow proper positioning of the annuloplasty ring 800 against the annulus.

Figure 8B:
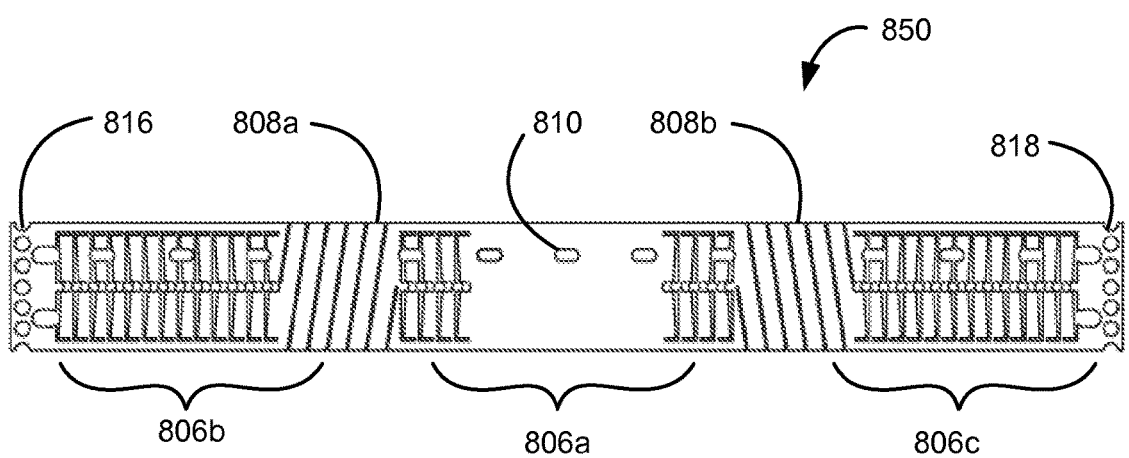
FIG. 8B is a schematic diagram of a cutting pattern used to form the annuloplasty ring shown in FIG. 8A according to certain embodiments.

FIG. 8B is a schematic diagram illustrating a cutting pattern 850 used for laser processing a hypotube to form the body member 802 of the annuloplasty ring 800 shown in FIG. 8A. The cutting pattern 850 corresponds to the entire body member 802 as if the body member 802 were cut along a longitudinal axis and unrolled. The cutting pattern 850 enables cutting the hypotube to form the plurality of anchor regions 806 and expansion regions 808. The cutting pattern 850 shown in FIG. 8B defines the configuration of the plurality of regions 806, 808 and how the regions 806, 808 interact with adjacent regions as the body member 802 transitions from the elongate insertion geometry to the annular operable geometry.

The cutting pattern 850 also enables cutting the body member 802 to form anchor windows 810 through which the plurality of anchors 804 are deployed. The cutting pattern 850 may also enable cutting the body member 802 to form one or more through holes 816, 818 at each end to allow one or more pins (not shown) to couple male and/or female components of the ring closure lock 812 to respective ends of the body member 802.

In certain embodiments, deployment of the anchors is accomplished using internal anchor members that are selectively movable within the body member of an annuloplasty ring. For example, FIGS. 9A, 9B, 9C, 9D, and 9E are simplified views of an internal anchor ribbon 900 and an internal anchor ribbon 902, each anchor ribbon including a plurality of anchors 904*a*, 904*b* (referred to collectively as anchors 904). The anchors 904 are integral to each anchor ribbon 900, 902. Each anchor ribbon 900, 902 includes two or more anchors 904. The anchors 904 may be affixed (e.g., laser welded) to the internal anchor ribbons 900, 902 or directly cut into the internal anchor ribbons 900, 902 (as discussed with respect to FIGS. 9A, 9B, and 9C). The anchors 904 may be similar to anchor 604 discussed above in reference to FIG. 8A. For example, the anchors 904 may be superelastic such that applying sufficient stress places the anchors 904 into an introduction configuration and releasing the stress allows the anchors 904 to resume their respective deployed configurations. The anchors 904 may be selectively deployed at a desired time (e.g., after the annuloplasty ring is properly positioned against the annulus of the heart valve). In certain embodiments, the superelastic property of the anchors 904 is used to self-propel the anchors 904 into the annulus of the heart valve. The superelastic property of the anchors 904, combined with the curvature of the anchors 904, causes the anchors 904 to spring into tissue with extra force.

In some embodiments, the anchors 904 are in the same plane as the anchor ribbons 900, 902. In other embodiments, the anchors deploy at an angle to the plane of the anchor ribbons 900, 902, such as 10° or 45°. Additionally, as shown in FIG. 9C, multiple anchor ribbons may be placed in parallel with each other to affect a more secure attachment of the ring to the native annulus.

The internal anchor ribbons 900, 902 may be slid (e.g., using wires or sutures accessible through the catheter) within the body member of the annuloplasty ring. To reduce friction between the internal anchor ribbons 900, 902 and the body member, certain embodiments include an internal glide ribbon 910. The internal glide ribbon 910 may include a low-friction material (e.g., as a coating or covering) such as PTFE or other polymer.

Figure 9A:
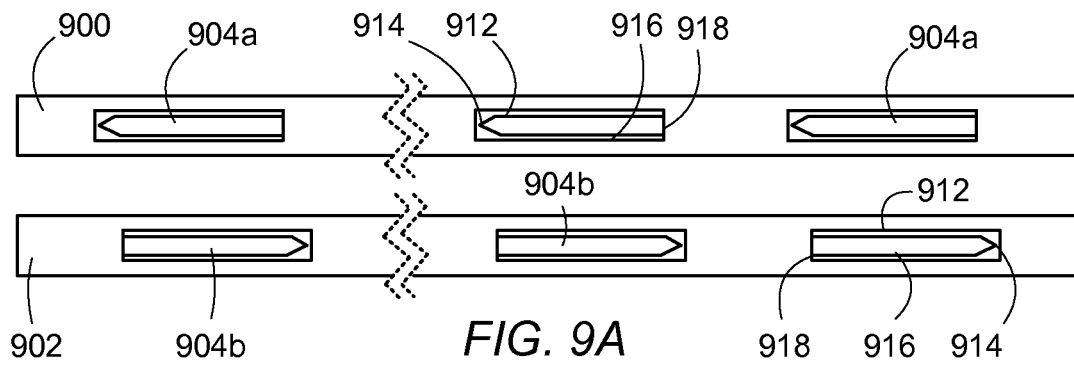
FIG. 9A is a simplified schematic diagram illustrating a top view of internal anchor ribbons according to certain embodiments.
Figure 9B:
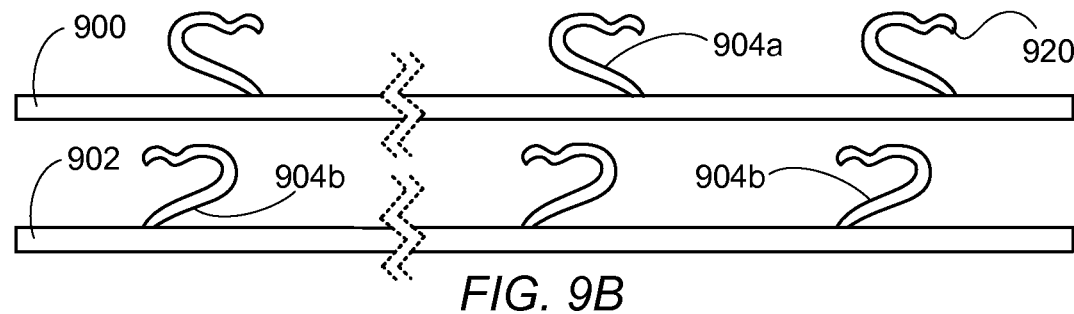
FIG. 9B is a simplified schematic diagram illustrating a side view of the internal anchor ribbons shown in FIG. 9A according to certain embodiments.
Figure 9C:
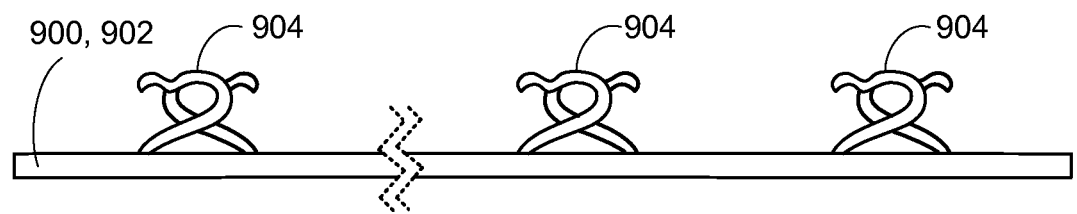
FIG. 9C is a simplified schematic diagram illustrating an overlapping side view of the internal anchor ribbons shown in FIG. 9B.
Figure 9D:
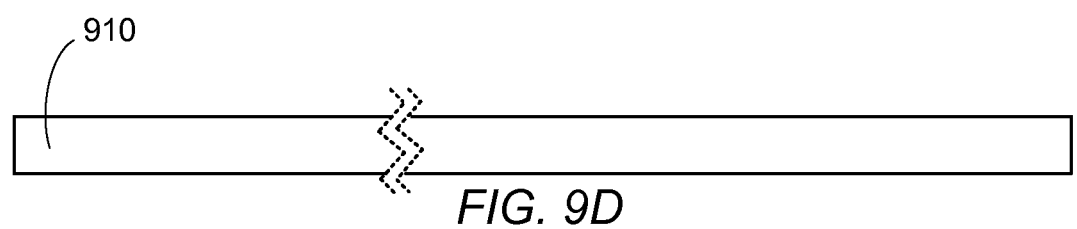
FIG. 9D is a simplified schematic diagram illustrating a top view of a glide ribbon according to certain embodiments.
Figure 9E:
FIG. 9E is a simplified schematic diagram illustrating a side view of the glide ribbon shown in FIG. 9D.

FIG. 9A is a schematic diagram illustrating a top view of the anchors 904 cut into the internal anchor ribbons 900, 902 shown in the elongate insertion geometry according to one embodiment. In this example, a laser is used to cut the anchors 904 along a first side 912, a second side 914 (e.g., in a pointed or tip shape), and a third side 916, while leaving a fourth side 918 of the anchor 904 uncut and attached to the internal anchor ribbons 900, 902. After cutting, the anchors 904 are heat set to the desired memorized shape for the deployed configuration. For example, FIG. 9B is a schematic diagram illustrating a side view of the internal anchor ribbons 900, 902 in the elongate insertion geometry and the anchors 904 in a deployed configuration according to one embodiment. The amount of curvature in the deployed configuration of the anchors 904 may depend on the particular application. In the example shown in FIG. 9B, the anchors 904 has a "wave" structure. Additionally, internal anchor ribbons 900, 902 are arranged so that the anchors 904*a* of internal anchor ribbon 900 point in the opposite direction from the anchors 904*b* of internal anchor ribbon 902. When deployed, the opposing anchors 904*a*, 904*b* provide improved anchoring when compared to anchors that all point in the same direction. FIG. 9C is a schematic diagram showing the internal anchor ribbons 900, 902 arranged side by side. When arranged side by side, the anchors 904 overlap, thereby providing improved anchoring. FIG. 9D is a schematic diagram illustrating a top view of the internal glide ribbon 910, and FIG. 9E is a schematic diagram illustrating a side view of the internal glide ribbon 910, in the elongate insertion geometry according to one embodiment.

In one embodiment, the anchor ribbons 900, 902 include a superelastic shape memory material (e.g., Nitinol) that is heat set to the same memorized annular shape as the body member 802 (shown in FIG. 8A as D-shaped). In addition, or in other embodiments, the internal glide ribbon 910 includes a superelastic shape memory material (e.g., Nitinol) that is heat set to the same memorized annular shape as the body member 802 (shown in FIG. 8A as D-shaped). Thus, certain embodiments include four D-shaped superelastic members (the body member 802, the internal anchor ribbons 900, 902, and the internal glide ribbon 910), which cooperate to shape and increase the rigidity of the ring 600.

Figure 10A:
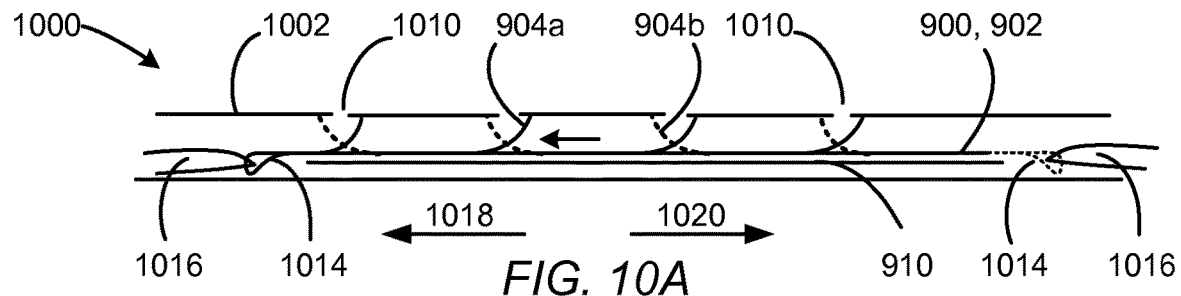
FIG. 10A is a simplified schematic diagram illustrating a cross-sectional side view of an annuloplasty ring before anchor deployment according to certain embodiments.
Figure 10B:
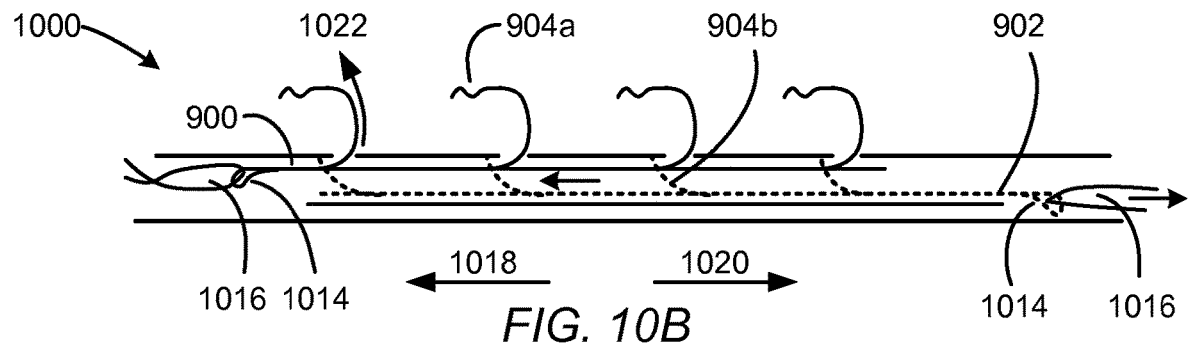
FIG. 10B is a simplified schematic diagram illustrating a cross-sectional side view of an annuloplasty ring during anchor deployment according to certain embodiments.

FIGS. 10A, 10B, and 100 are simplified schematics illustrating cross-section side views of an annuloplasty ring 1000 before (FIG. 10A), partway through (FIG. 10B) and after (FIG. 10C) deployment of the anchors 904 shown in FIG. 9C according to one embodiment. Artisans will recognize from the disclosure herein that the anchors 904 are generally deployed when the ring 1000 is in the annular operable geometry. The ring 1000 may be similar to the annuloplasty ring 800 discussed above in reference to FIG. 8A.

The illustrated ring 1000 includes an outer tube 1002 (e.g., the body member 802 shown in FIG. 8A) including a plurality of anchor deployment windows 1010. During the manufacturing of the ring 1000 and before the ring 1000 is loaded into the catheter, the internal anchor ribbons 900, 902 and the internal glide ribbon 910 are inserted into the outer tube 1002 in a position where the anchors 904 are prevented from exiting through the windows 1010. As shown in FIG. 10A, inserting the internal anchor ribbons 900, 902 into the outer tube 1002 prevents the anchors 904 from assuming their fully curved deployed configuration. In the illustrated embodiment, each anchor 904a of anchor ribbon 900 share an anchor deployment window 1010 with an anchor 904b of anchor ribbon 902. In other embodiments, every anchor 904a, 904b has its own anchor deployment window 1010.

Figure 10C:
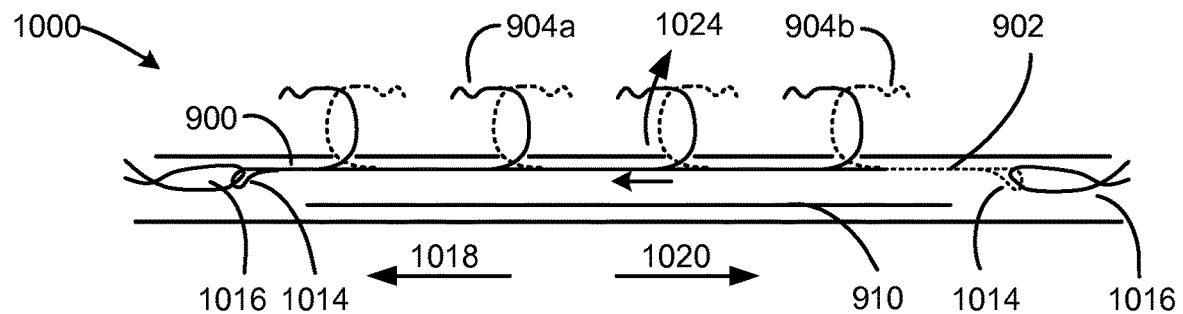
FIG. 10C is a simplified schematic diagram illustrating a cross-sectional side view of an annuloplasty ring after anchor deployment according to certain embodiments.

For deploying the anchors 904, the internal anchor ribbons 900, 902 may include (or may be attached to) a hook or loop 1014 for engaging a wire or suture 1016 that may be pulled by a user through the catheter. As the anchors 904a of the internal anchor ribbon 900 point in the opposite direction from the anchors 904b of the internal anchor ribbon 902, the anchor ribbon 900 is pulled in the direction of arrow 1018 while the anchor ribbon 902 is pulled in the opposite direction (e.g., in the direction of arrow 1020). By pulling the anchor ribbons 900, 902 the tips of each anchor 904 move to a corresponding window 1010. In certain embodiments, the anchors 904 and windows 1010 are arranged such that the tip of each anchor 904 reaches its respective window 1010 at substantially the same time as the other anchors reach their windows. As shown in FIG. 10B, once the tips of the anchors 904a of the anchor ribbon 900 reach the respective windows 1010, the superelasticity of the anchors 904a propels the internal anchor ribbon 900 in the opposite direction (shown by arrow 1020) as the anchors 904a spring out through the windows 1010 (as indicated by arrow 1022) to resume their curved configurations, thereby driving the anchors 904a into surrounding tissue (e.g., the heart valve annulus). As shown in FIG. 10C, once the tips of the anchors 904b of the anchor ribbon 902 reach the respective windows 1010, the superelasticity of the anchors 904b propels the internal anchor ribbon 902 in the opposite direction (shown by arrow 1018) as the anchors 904 spring out the windows 1010 (as indicated by arrow 1024) to resume their curved configurations, thereby driving the anchors 904b into surrounding tissue (e.g., the heart valve annulus). Thus, the superelasticity of the anchors 904 allows the anchors 904 to be self-propelled into the tissue adjacent or proximate to the ring 1000. While the sequence of FIGS. 10A, 10B, and 10C shows the anchor ribbon 900 deploying before the anchor ribbon 902, artisans will recognize that the anchor ribbon 902 may be deployed first, or the anchor ribbons 900, 902 may be deployed simultaneously.

Figure 10D:
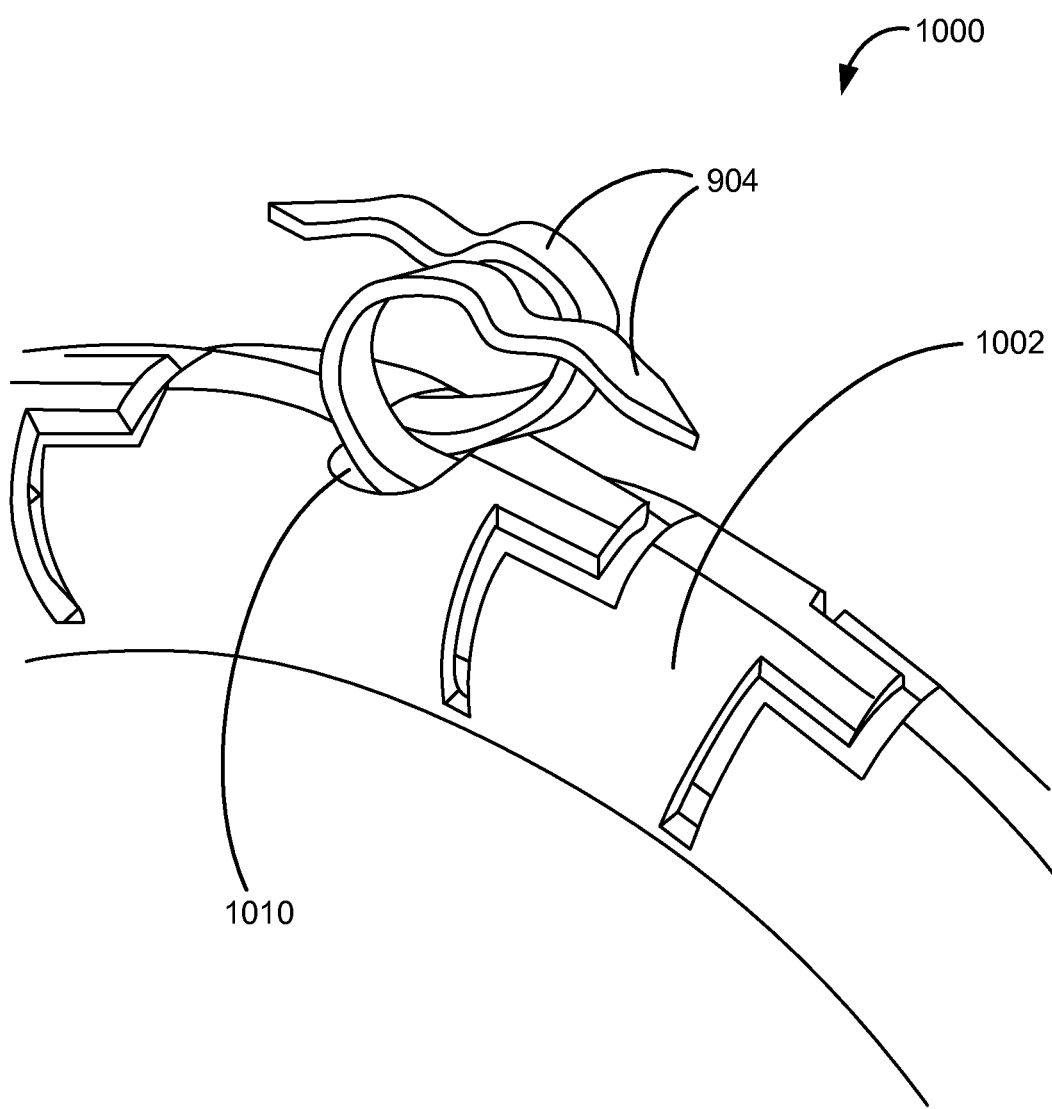
FIG. 10D is a perspective view of a portion of an annuloplasty ring after anchor deployment according to certain embodiments.

FIG. 10D is a perspective view of a portion of the annuloplasty ring 1000 shown in FIGS. 10A, 10B, and 10C with a pair of deployed anchors 904 according to one embodiment. The outer tube 802 may include the windows 810 (one window shown in FIG. 10D) described above and schematically represented in FIGS. 10A, 10B, and 100. In certain embodiments, the deployed anchors 904 form an angle with a plane of the ring 1000 to provide the anchors 904 with improved access to the valve annulus when the ring is positioned against the valve annulus. During anchor deployment, the plane of the ring 1000 is substantially parallel to the plane of the valve annulus.

In certain embodiments, deployment of the anchors is accomplished using a plurality of internal anchor members that are independently deployable within the body member of an annuloplasty ring. For example, FIGS. 11A, 11B, 11C, and 11D are perspective views of an annuloplasty ring 1100 with separately deployable anchor members according to certain embodiments. The annuloplasty ring 1100 may be similar to annuloplasty rings 800, 1000 discussed above in reference to FIGS. 8A, and 10A, 10B, 10C, and 10D. The annuloplasty ring 1100 includes an outer tube or body member 1102, a plurality of anterior anchors 1104a, a plurality of first posterior anchors 1104b, a plurality of second posterior anchors 1104c, a plurality of anterior anchor windows 1106a, a plurality of first posterior anchor windows 1106b, a plurality of second posterior anchor windows 1106c, an anterior anchor ribbon 1110, a first posterior anchor ribbon 1112, and a second posterior anchor ribbon 1114, each anchor ribbon including a plurality of anchors 1104. The anterior anchors 1104a, first posterior anchors 1104b, and second posterior anchors 1104c (collectively referred to as anchors 1104) are integral to their respective anchor ribbons 1110, 1112, 1114. The anchors 1104 may be affixed (e.g., laser welded) to the anchor ribbons 1110, 1112, 1114, respectively, or directly cut into the anchor ribbons 1110, 1112, 1114. Each of the anchor ribbons 1110, 1112, 1114 includes two or more anchors 1104. The anchors 1104 may be similar to anchors 804 discussed above in reference to FIG. 8A. For example, the anchors 1104 may be superelastic such that applying sufficient stress places the anchors 1104 into an introduction configuration and releasing the stress allows the anchors 1104 to resume their respective deployed configurations. The anchors 1104 may be selectively deployed at a desired time (e.g., after the annuloplasty ring 1100 is properly positioned against the annulus of the heart valve). In certain embodiments, the superelastic property of the anchors 1104 is used to self-propel the anchors 1104 into the annulus of the heart valve. The superelastic property of the anchors 1104, combined with the curvature of the anchors 1104 causes the anchors 1104 to spring into tissue with extra force. The anterior anchor windows 1106a, first posterior anchor windows 1106b, and second posterior anchor windows 1106c (collectively referred to as anchor windows 1106) allow the anchors 1104 to pass through the body member 1102 into the annular tissue.

In some embodiments, the anchors 1104 are in the same plane as the anchor ribbons 1110, 1112, 1114. In other embodiments, the anchors deploy at an angle to the plane of the anchor ribbons 1110, 1112, 1114, such as 10° or 45°. Additionally, multiple anchor sections may be placed in parallel with each other to affect a more secure attachment of the ring to the native annulus.

Figure 11B:
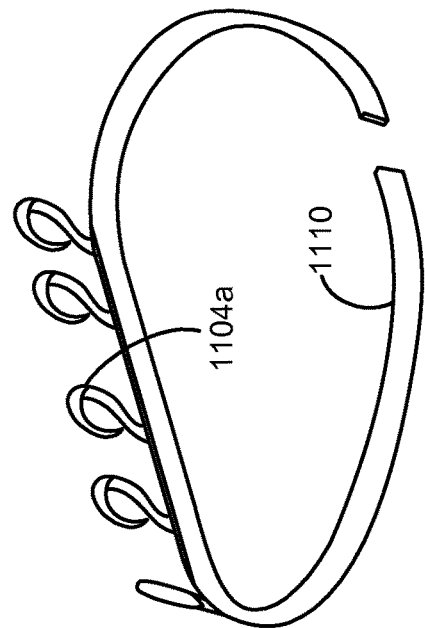
FIG. 11B is a perspective view of a separately deployable anchor member according to certain embodiments.
Figure 11D:
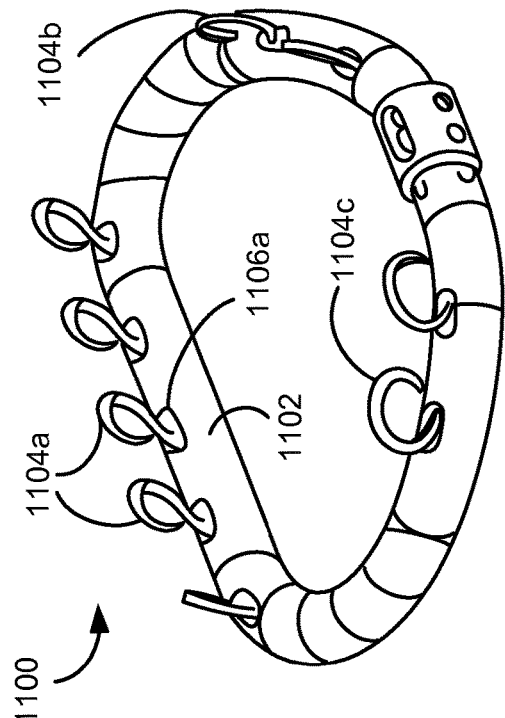
FIG. 11D is a perspective view of an annuloplasty ring with separately deployable anchor members with the anchors in a deployed configuration according to certain embodiments.
Figure 11A:
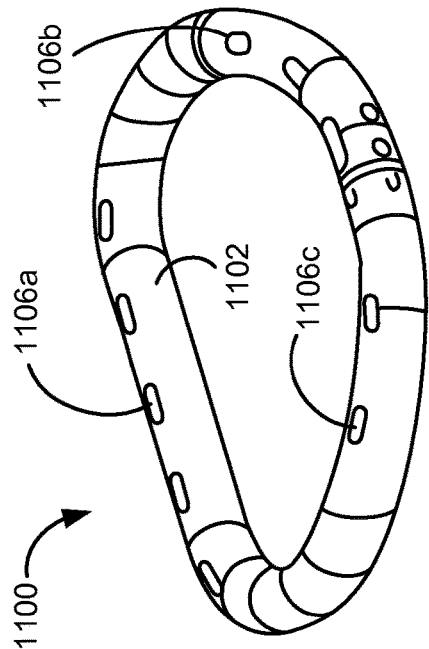
FIG. 11A is a perspective view of an annuloplasty ring with separately deployable anchor members with the anchors in an introduction configuration according to certain embodiments.

FIG. 11A shows the ring 1100 in the operative configuration with the anchors 1104 in the introduction configuration. FIG. 11D shows the ring 1100 in the operative configuration with the anchors 1104 in the deployed configuration. Artisans will recognize from the disclosure herein that the anchors 1104 are generally deployed when the ring 1100 is in the annular operable geometry and in proximity to the heart valve annulus. The amount of curvature in the deployed configuration of the anchors 1104 may depend on the particular application. In the example shown in FIGS. 11B, 11C, and 11D, the anchors 1104 have a curled structure such that the prong or tip points at the anchor ribbons 1110, 1112, 1114. When deployed, the curled anchors provide secure anchoring in the annular tissue.

Figure 11C:
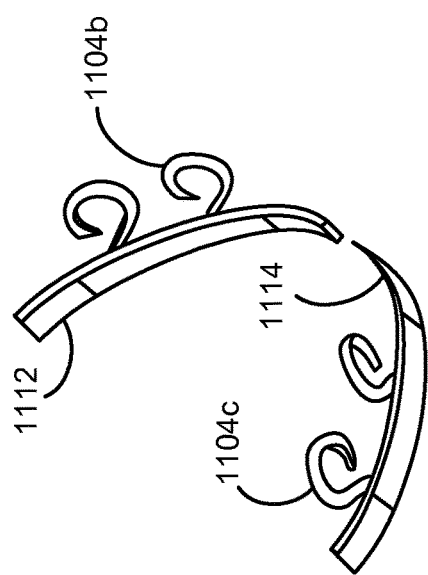
FIG. 11C is a perspective view of a pair of separately deployable anchor members according to certain embodiments.

FIG. 11B shows the anterior anchor ribbon 1110 with the anterior anchors 1104a arranged in the deployed, operative configuration. FIG. 11C shows the first posterior anchor ribbon 1112 and the second posterior anchor ribbon 1114 with the first posterior anchors 1104b and the second posterior anchors 1104c arranged in the deployed, operative configuration. The anchor ribbons 1110, 1112, 1114 may be slid (e.g., using wires or sutures accessible through the catheter) within the body member 1102 of the annuloplasty ring 1100. To reduce friction between the anchor ribbons 1110, 1112, 1114 and the body member, certain embodiments include an internal glide ribbon (not shown) that may includes a low-friction material (e.g., as a coating or covering) such as PTFE or other polymer. The anchor ribbons 1110, 1112, 1114 include a superelastic shape memory material (e.g., Nitinol) that is heat set to the same memorized annular shape as the body member 1102 (shown in FIG. 11D as D-shaped). In certain embodiments, the internal glide ribbon includes a superelastic shape memory material (e.g., Nitinol) that is heat set to the same memorized annular shape as the body member 1102. Thus, certain embodiments include five D-shaped superelastic members (the body member 1102, the anchor ribbons 1110, 1112, 1114, and the internal glide ribbon), which cooperate to increase the rigidity of the ring 1100.

The body member 1102 includes a plurality of anchor deployment windows 1106. During the manufacturing of the ring 1100, and before the ring 1100 is loaded into the catheter, the anchor ribbons 1110, 1112, 1114 are inserted into the body member 1102 in a position where the anchors 1104 are prevented from exiting through the anchor windows 1106. This is referred to as the introduction configuration. As shown in FIG. 11A, the body member 1102 prevents the anchors 1104 from assuming their fully curved deployed configuration.

For deploying the anchors 1104, the anchor ribbons 1110, 1112, 1114 may include (or may be attached to) a hook or loop (not shown) for engaging a wire or suture that may be pulled by a user through the catheter. Pulling the anchor ribbons 1110, 1112, 1114 moves the tips of each anchor 1104 to a deployment window 1106. In certain embodiments, the anchors 1104 and windows 1106 are arranged such that the tip of each anchor 1104 on an anchor ribbon (e.g., anterior anchor ribbon 1110) reaches its respective window 1106 at substantially the same time as the other anchors 1104 on the anchor ribbon reach their window 1106. Once the tips of the anchors 1104 of an anchor ribbon reach the respective windows 1106, the superelasticity of the anchors 1104 springs them out through the windows 1106 to resume their curved configurations, thereby driving the anchors 1104 into surrounding tissue (e.g., the heart valve annulus). Thus, the superelasticity of the anchors 1104 allows the anchors 1104 to be self-propelled into the tissue adjacent, or proximate, to the ring 1100.

As seen in FIGS. 12A, 12B, 12C, and 12D, the anchor ribbons may be deployed in an independent manner because each anchor ribbon 1110, 1112, or 1114 is independent of the others. Accordingly, the anchors 1104 may be selectively deployed from different locations of the annuloplasty ring 1100 at different times.

Figure 12A:
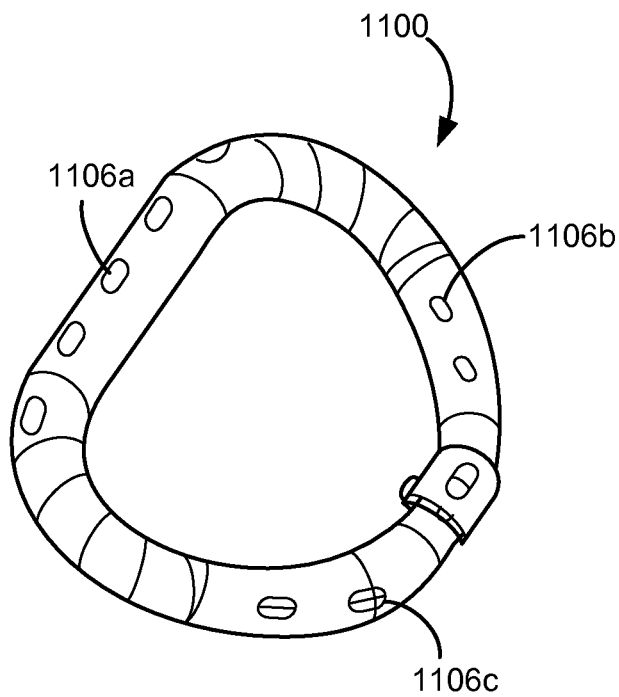
FIG. 12A is a perspective view of an annuloplasty ring with independently deployable anchor members before anchor deployment according to certain embodiments.

FIG. 12A shows the annuloplasty ring 1100 in the operative configuration with the anchors 1104 in the introduction configuration. The annuloplasty ring 1100 is maneuvered into position near the heart valve annulus before the anchors 1104 are deployed.

Figure 12B:
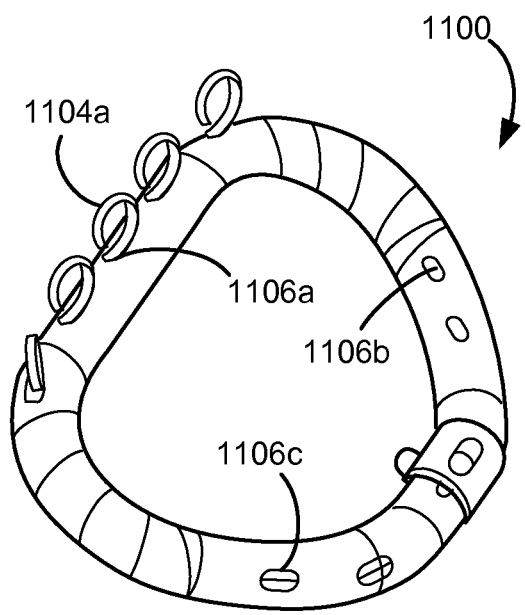
FIG. 12B is a perspective view of an annuloplasty ring with independently deployable anchor members during anchor deployment according to certain embodiments.

FIG. 12B shows the annuloplasty ring 1100 with the anterior anchors 1104a deployed. To transition from FIG. 12A to FIG. 12B, the anterior anchor ribbon 1110 is pulled within the body member 1102 until the anterior anchors 1104a reach the anterior deployment windows 1106a. Upon reaching the anterior deployment windows 1106a, the anterior anchors 1104a self-propel into the deployment configuration.

Figure 12C:
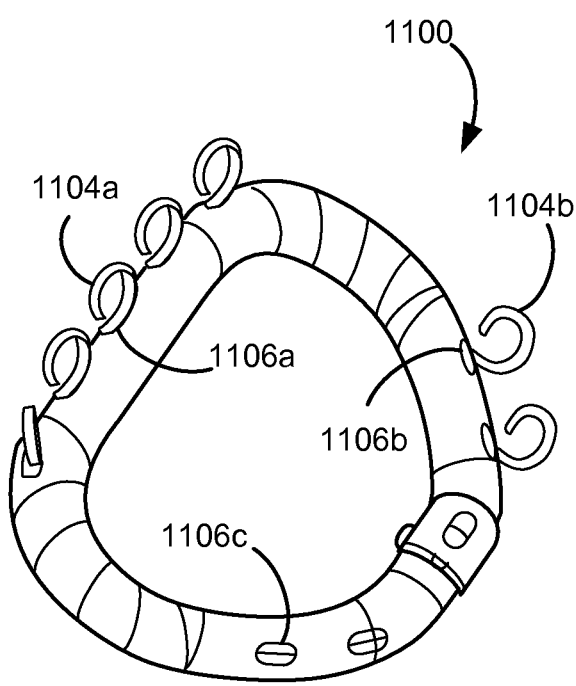
FIG. 12C is a perspective view of an annuloplasty ring with independently deployable anchor members during anchor deployment according to certain embodiments.

FIG. 12C shows the annuloplasty ring 1100 with the anterior anchors 1104a and the first posterior anchors 1104b deployed. To transition from FIG. 12B to FIG. 12C, the first posterior anchor ribbon 1112 is pulled within the body member 1102 until the first posterior anchors 1104b reach the first posterior deployment windows 1106b. Upon reaching the first posterior deployment windows 1106b, the first posterior anchors 1104b self-propel into the deployment configuration.

Figure 12D:
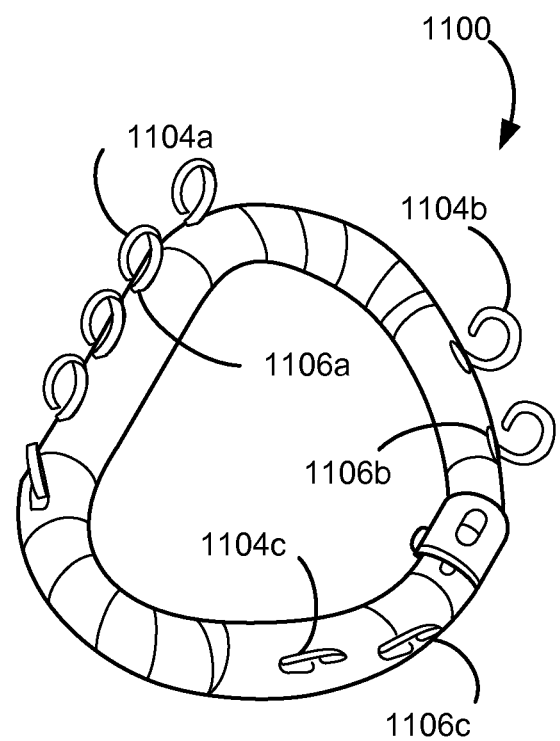
FIG. 12D is a perspective view of an annuloplasty ring with independently deployable anchor members after anchor deployment according to certain embodiments.

FIG. 12D shows the annuloplasty ring 1100 with the anterior anchors 1104a, the first posterior anchors 1104b and the second posterior anchors 1104c deployed. To transition from FIG. 12C to FIG. 12D, the second posterior anchor ribbon 1114 is pulled within the body member 1102 until the second posterior anchors 1104c reach the second posterior deployment windows 1106c. Upon reaching the second posterior deployment windows 1106c, the second posterior anchors 1104c self-propel into the deployment configuration.

Although the sequence of FIGS. 12B, 12C, and 12D shows the anterior anchors 1104a deploying first, then the first posterior anchors 1104b, and finally the second posterior anchors 1140c, artisans will recognize that the anchors 1104a, 1104b, 1104c may be deployed in any order, including simultaneously.

Example Anchor Shapes and Designs

FIG. 13 is a view of various anchor shapes that may be used with the disclosed trans-catheter annuloplasty rings. Anchor shapes 1300, 1320, and 1330 have curved geometries and may be formed from superelastic material, such as Nitinol, so that they self-propel into annulus tissue. The variations in curvature and shape allow for the anchors to deploy into the annular tissue at differing depths. Anchor shape 1310 has a "wavy" geometry. The wave shape gives better grip into the tissue in certain environments. Anchor shape 1340 has a straight geometry and may be propelled into annular tissue through application of mechanical force (e.g., by inflating a balloon behind anchor 1340 or in the center of the annuloplasty ring). Artisans will recognize from the disclosure herein that combinations of barb designs and/or deployed configurations may also be used. In some embodiments, all of the anchors of an annuloplasty rings are of the same shape. In other embodiments, an annuloplasty ring may employ a plurality of anchor shapes. For example, one anchor shape may be used to anchor the annuloplasty ring into the anterior portion of the heart valve annulus while a different anchor shape may be used to anchor the annuloplasty ring into the posterior portion of the heart valve annulus. The selected anchor shape or geometry may depend on the particular application.

FIG. 14 is a view of various anchor designs that may be used with the disclosed trans-catheter annuloplasty rings. The different designs may be employed to give an anchor greater flexibility or strength, and/or to enhance anchoring within the heart tissue. Controlling the strength of the anchors provides improved tissue penetration by using the strength of the anchors as a driving mechanism. Controlling the elasticity of the anchors allows the anchors to recover from the configuration inside the catheter, when the anchors are in their original cut patter, to their final (deployed) configuration after heat treatment. Anchor design 1400 employs ovoid or rounded-rectangular cutouts along the length of the anchor to provide the anchor with high strength and low elasticity. Anchor design 1410 employs wave cutouts along the length of the anchor to provide the anchor with medium strength and high elasticity (e.g., so as to better act like a spring). Anchor design 1420 employs three offset lines of ovoid or rounded-rectangular cutouts along the length of the anchor to provide the anchor with medium strength and high elasticity (e.g., so as to better act like a spring). Anchor design 1430 employs ovoid or rounded-rectangular cutouts along the length of the anchor. The cutouts of anchor design 1430 are oriented perpendicularly to the length of the anchor (and to the cutouts of anchor design 1400). Anchor design 1440 employs a single ovoid or rounded-rectangular cutout along the length of the anchor to provide medium strength and medium elasticity to the anchor. Anchor design 1450 employs two ovoid or rounded-rectangular cutouts along the length of the anchor. Artisans will recognize from the disclosure herein that combinations of barb designs and/or deployed configurations may also be used. The selected anchor design may depend on the particular application.

Example Deployment Embodiments

Figure 15A:
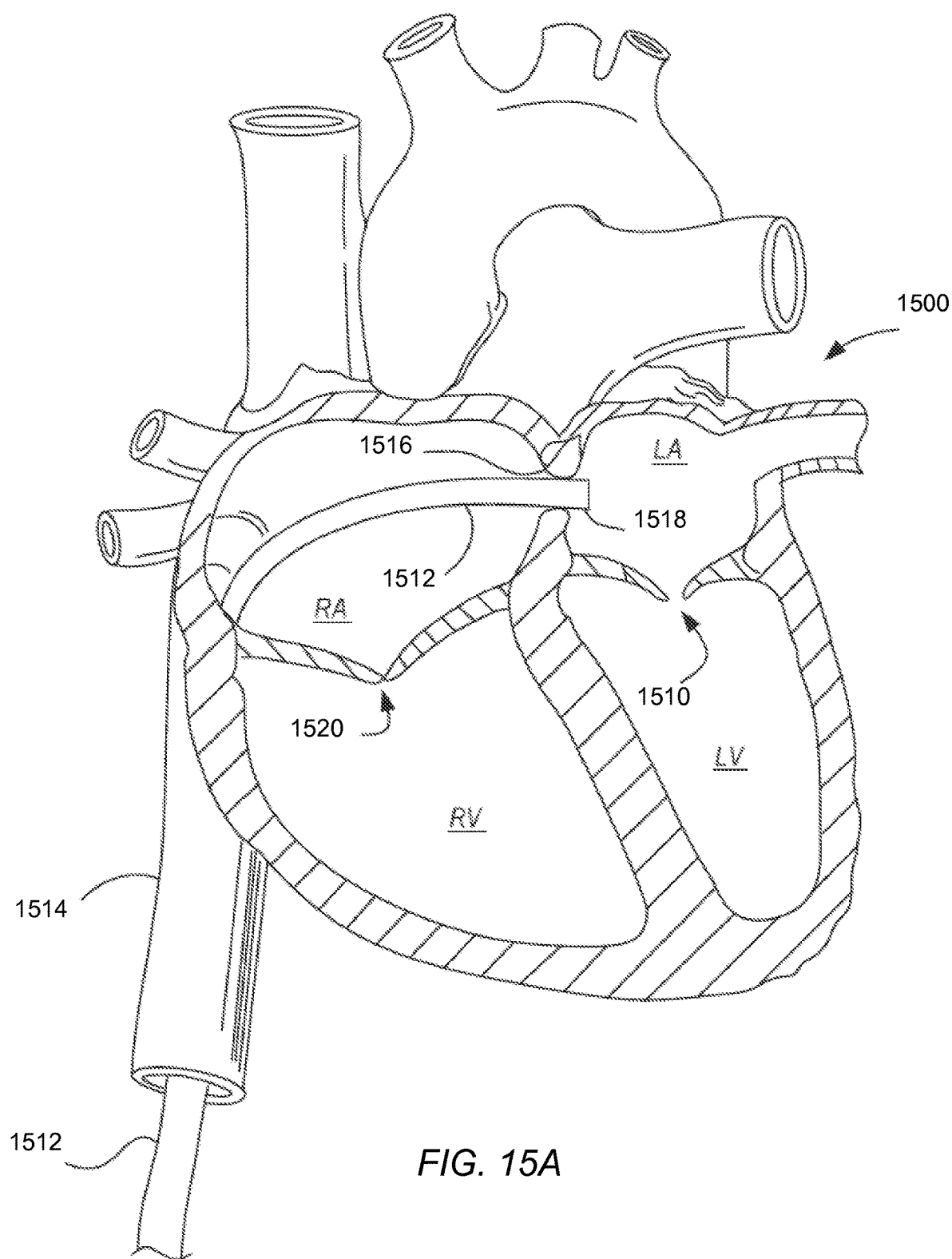
FIG. 15A is a schematic diagram illustrating a trans-septal approach for endovascular delivery of an annuloplasty ring to the mitral valve of a heart according to one embodiment.

As discussed above, the annuloplasty ring embodiments disclosed herein are configured for percutaneous transcatheter delivery and fixation to heart valves. The annuloplasty rings may be delivered through a catheter to the mitral valve, for example, using a trans-septal approach, a retrograde approach, or a trans-apical approach. For example, FIG. 15A is a schematic diagram illustrating a trans-septal approach for endovascular delivery of an annuloplasty ring (not shown) to the mitral valve 1510 of a heart 1500 according to one embodiment. For illustrative purposes, a partial cross-section of the heart 1500 is illustrated to show the right atrium RA, right ventricle RV, left atrium LA, and left ventricle LV. For clarity, certain features (e.g., papillary muscles and chordae tendineae) are not shown. In the trans-septal approach shown in FIG. 15A, the left atrium LA is approached by advancement of a catheter 1512 through the inferior vena cava 1514, into the right atrium RA, across the interatrial septum 1516, and into the left atrium LA. The annuloplasty ring may then be delivered through the catheter 1512 into the atrium and anchored to the annulus of the mitral valve 1510.

As shown in FIG. 15A, the catheter 1512 is delivered percutaneously into the heart 1500. A guiding sheath (not shown) may be placed in the vasculature system of the patient and used to guide the catheter 1512 and its distal end 1518 to a desired deployment site. In some embodiments, a guide wire (not shown) is used to gain access through the superior or inferior vena cava 1514, for example, through groin access for delivery through the inferior vena cava 1514. The guiding sheath may be advanced over the guide wire and into the inferior vena cava 1514 shown in FIG. 15A. The catheter 1512 may be passed through the right atrium RA and toward the interatrial septum 1516. Once the distal end 1518 of the catheter 1512 is positioned proximate to the interatrial septum 1516, a needle or piercing member (not shown) is advanced through the catheter 1512 and used to puncture the fossa ovalis or other portion of the interatrial septum 1516. In some embodiments, the catheter 1512 is dimensioned and sized to pass through the fossa ovalis without requiring a puncturing device. That is, the catheter 1512 may pass through the natural anatomical structure of the fossa ovalis into the left atrium LA.

Similarly, any chamber (LV, RV, LA, RA) of the heart 1500 may be approached through the inferior vena cava 1514. For example, the right ventricle RV may be approached through the inferior vena cava 1514, into the right atrium RA, and through the tricuspid valve 1520. A variety of other endovascular approaches may also be used.

Figure 15B:
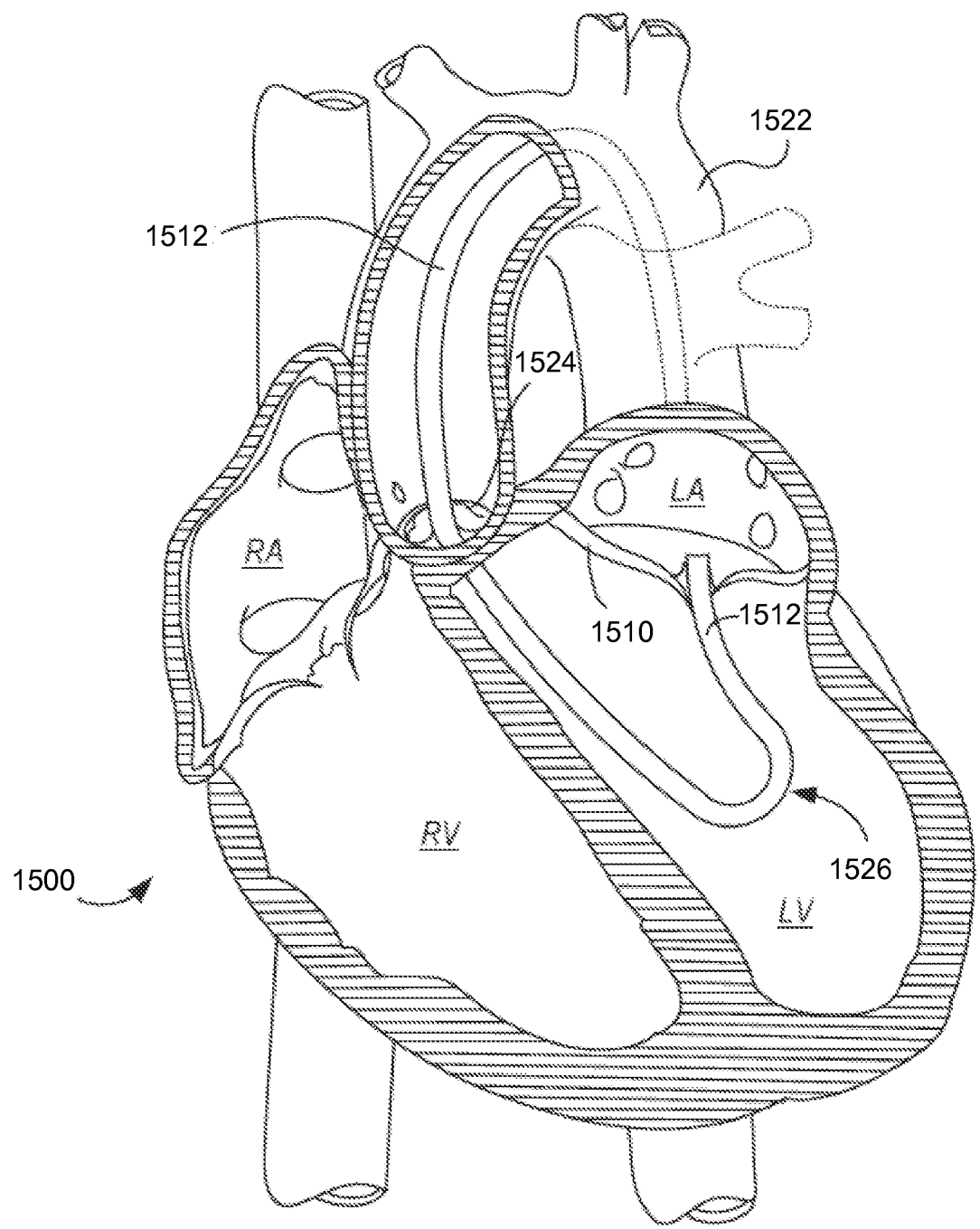
FIG. 15B is a schematic diagram illustrating an example retrograde approach of an annuloplasty ring to the mitral valve of a heart according to another embodiment.

FIG. 15B is a schematic diagram illustrating an example retrograde approach of an annuloplasty ring (not shown) to the mitral valve 1510 of a heart 1500 according to another embodiment. In FIG. 15B, a femoral approach is shown wherein the delivery catheter 1512 is advanced through the aorta 1522 and the aortic valve 1524. Typically, the catheter 1512 is advanced through a sheath positioned within the femoral artery (not shown). Under fluoroscopy or other methods of guidance, the distal end of the catheter 1512 is guided within the left ventricle LV and turned (e.g., as shown with a "U-turn" 1526) within the left ventricle LV so as to pass through the leaflets of the mitral valve 1510 and into the left atrium LA. After verification of the appropriate positioning of the catheter 1512, a guide wire (not shown) may be inserted through the catheter 1512 into the left atrium LA, which may then be used to guide one or more other catheters into the left atrium LA for delivering and anchoring the annuloplasty ring to the annulus of the mitral valve 1510.

Figure 15C:
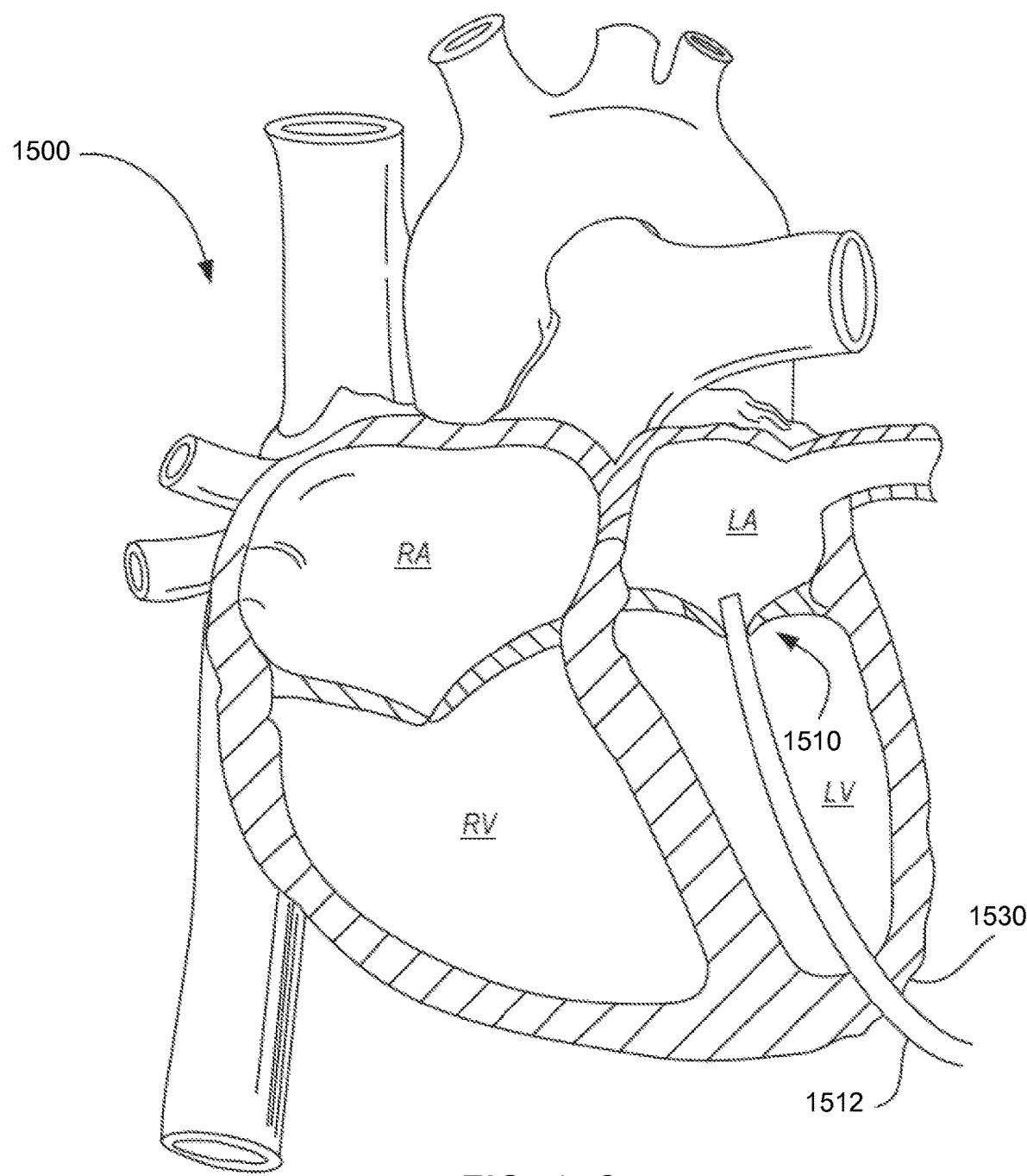
FIG. 15C is a schematic diagram illustrating an example trans-apical approach of an annuloplasty ring to the mitral valve of a heart according to another embodiment.

FIG. 15C is a schematic diagram illustrating an example trans-apical approach of an annuloplasty ring (not shown) to the mitral valve 1510 of a heart 1500 according to another embodiment. In this example, the catheter 1512 is shown passing through the apex 1530 of the heart 1500, through the left ventricle LV, through the leaflets of the mitral valve 1510, and into the left atrium. The annuloplasty ring may be delivered through the catheter 1512 into the left atrium LA and anchored to the annulus of the mitral valve 1510. In one embodiment, a needle or trocar may be used to puncture through the apex 1530 to create a small opening through which a guide wire (not shown) can be inserted through the left ventricle LV into the left atrium LA. Then, the guide wire may be used to guide successively larger and stiffer catheters so as to gradually increase the size of the opening in the apex 1530 of the heart 1500.

In some embodiments, an annuloplasty ring will comprise a pivot used to rotate the annuloplasty ring after it exits the catheter within the heart to align the plane of the annuloplasty ring (in the annular operable geometry) with the plane of the heart valve. The annuloplasty ring is pushed from the catheter in a direction that is substantially perpendicular to the plane of the heart valve (e.g., parallel to the direction of blood flow). Upon exiting the catheter, annuloplasty ring may be rotated via the pivot to allow the annuloplasty ring to be properly positioned against the annulus. In some embodiments, the annuloplasty ring is expanded at one or more expansion region(s) and pressed against the valve annulus (e.g., using a balloon) before deploying the anchors. The act of deploying the anchors drives the anchors into the tissue. Fluoroscopy, ultrasound, and/or other imaging techniques may be used to assist in proper positioning of the annuloplasty ring against the heart valve annulus.

Prior to deploying the anchors, the annuloplasty ring may be adjusted in the anterior-posterior (A-P) direction to for proper placement. Examples of an annuloplasty ring adjustable in the A-P direction are provided in U.S. patent application Ser. No. 13/779,478. After the anchors are deployed into the annulus tissue, the annuloplasty ring is allowed to contract thereby reducing the heart valve annulus dimensions and reducing regurgitation through the heart valve.

Figure 16A:
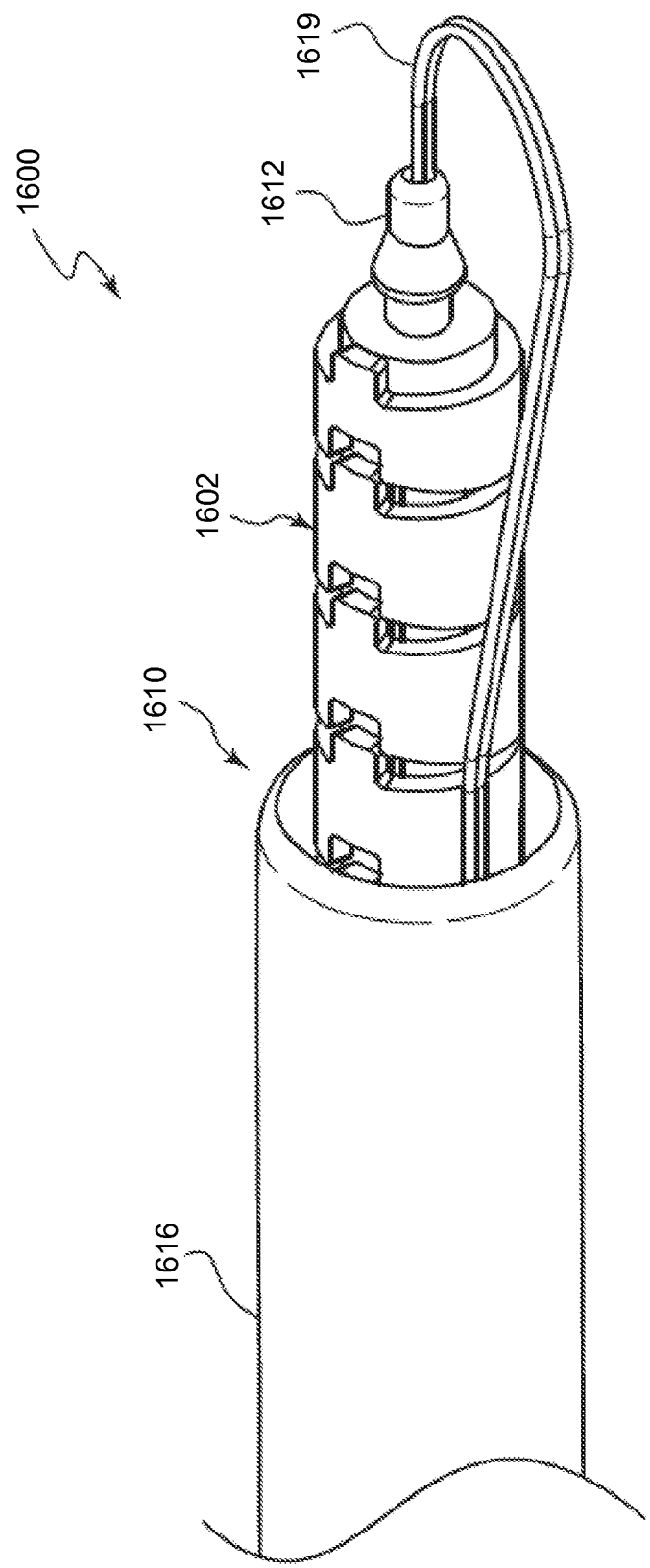
FIG. 16A is a perspective view of an annuloplasty ring in the elongate insertion geometry and partially deployed from the distal end of a delivery catheter in a first deployment stage according to certain embodiments.

FIGS. 16A, 16B, 16C, and 16D are schematic diagrams illustrating transcatheter delivery of an annuloplasty ring 1602 from a delivery system 1600 according to certain embodiments. FIG. 16A illustrates a perspective view of a distal end 1610 of the delivery system 1600. FIG. 16A is a perspective view of the annuloplasty ring 1602 in the elongate insertion geometry and partially deployed from the distal end 1610 of a delivery catheter 1614 in a first deployment stage. In the first stage, the annuloplasty ring 1602 may be still substantially in the elongate insertion geometry. As shown in FIG. 16A, a first suture 1619 for snapping together the ends of the annuloplasty ring 1602 passes through a male snap 1612 of a ring closure lock 1650 (shown in FIG. 16C).

Figure 16B:
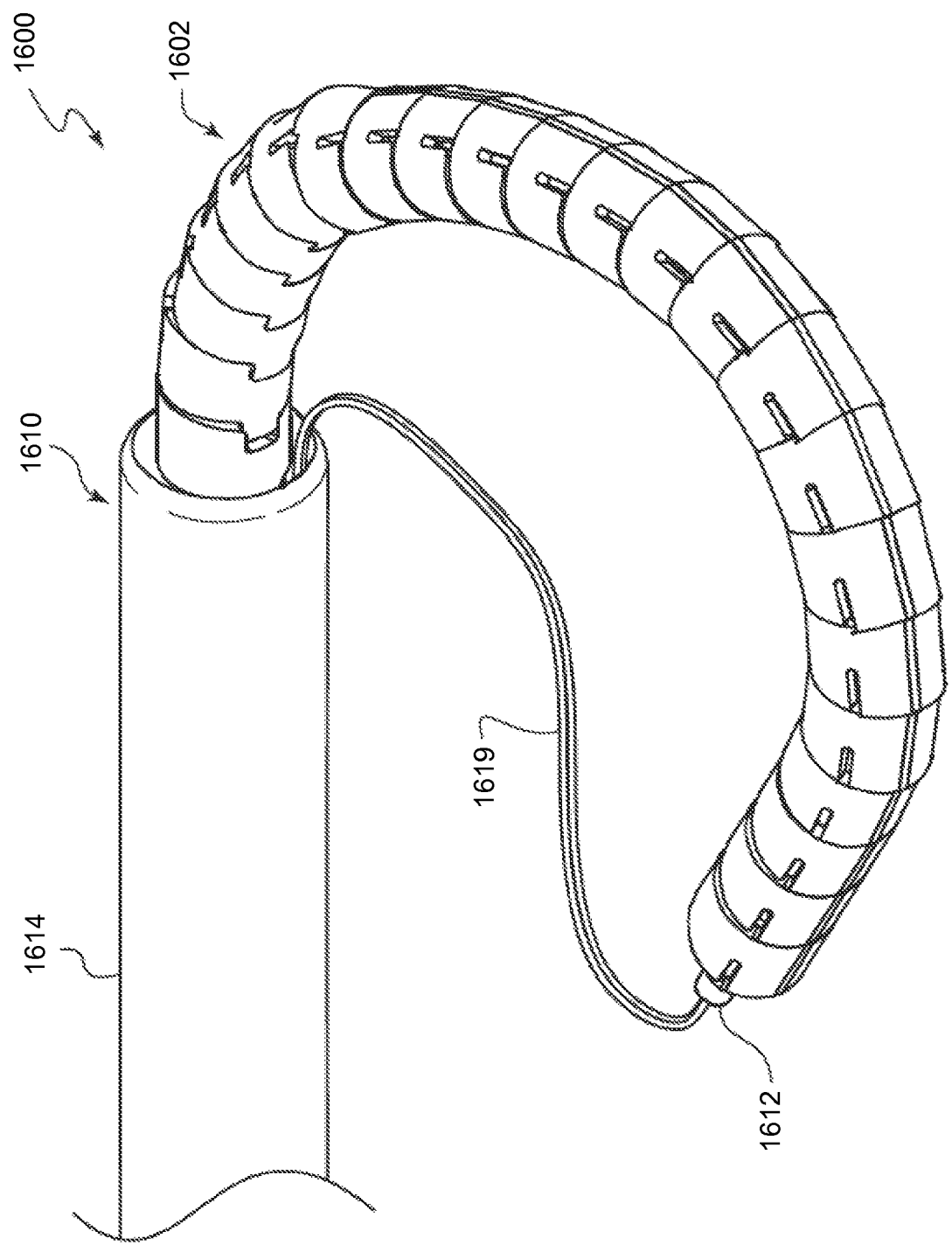
FIG. 16B is a perspective view of an annuloplasty ring in a second stage of partial deployment from the delivery catheter.

FIG. 16B is a perspective view of the annuloplasty ring 1602 in a second stage of partial deployment from the delivery catheter 1614. In the second stage, the portion of the annuloplasty ring 1602 that has exited the delivery catheter 1614 has begun to transition (due to the shape memory materials used in the annuloplasty ring 1602) from the elongate insertion geometry to the annular operable geometry.

Figure 16C:
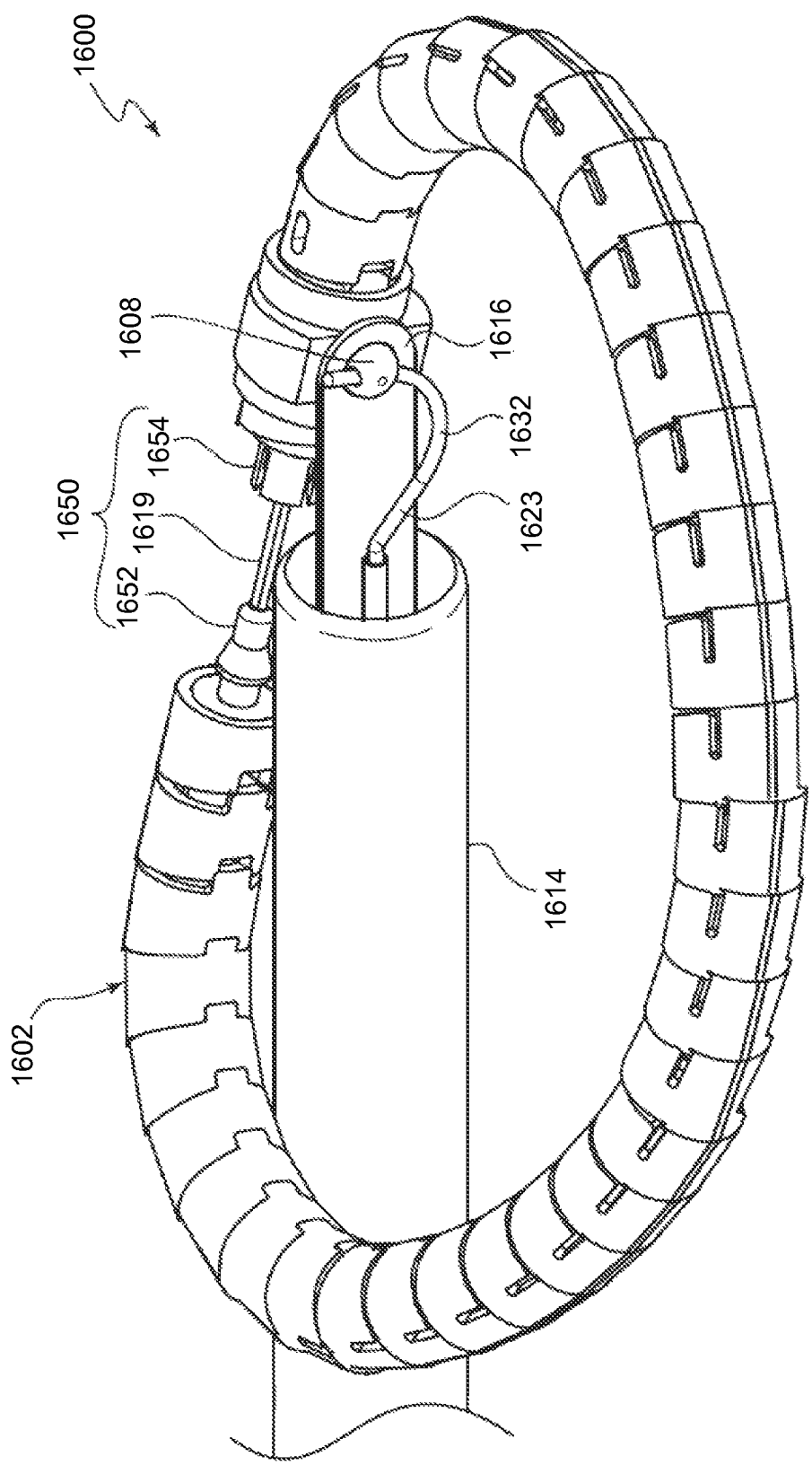
FIG. 16C is a perspective view of an annuloplasty ring in a third stage of deployment from the delivery catheter.

FIG. 16C is a perspective view of the annuloplasty ring 1602 in a third stage of deployment in which a ring shuttle 1616 of the delivery system 1600 has substantially pushed the annuloplasty ring 1602 out of the delivery catheter 1614, but the plane of the annuloplasty ring 1602 is still aligned with (e.g., approximately parallel to) the longitudinal axis of the delivery catheter 1614. In FIG. 16C, the annuloplasty ring 1602 may be in a configuration, for example, immediately before a ring deployment wire 1623 cooperates with the pivot 1608 to rotate the annuloplasty ring 1602 (see FIG. 16D). In the configuration shown in FIG. 16C, the distal end of the ring deployment wire 1623 includes a bend or hook 1632 as it passes through a hole in the pivot 1608. The ring deployment wire 1623 includes a superelastic shape memory material (e.g., Nitinol), and bending the distal end of the ring deployment wire 1623 into the hook 1632 shape spring loads the annuloplasty ring 1602 within the outer jacket delivery catheter 1614 such that the annuloplasty ring 1602 automatically rotates about the pivot 1608 upon exiting the outer jacket delivery catheter 1614. At this third stage of deployment, the hook 1632 shape formed in the superelastic ring deployment wire 1623 is ready to unload (return to a heat-set memorized straight configuration) as soon as the delivery catheter 1614 no longer prevents it from doing so. The suture 1619 may be utilized to draw together the male components 1652 and female components 1654 of a ring closure lock 1650.

Figure 16D:
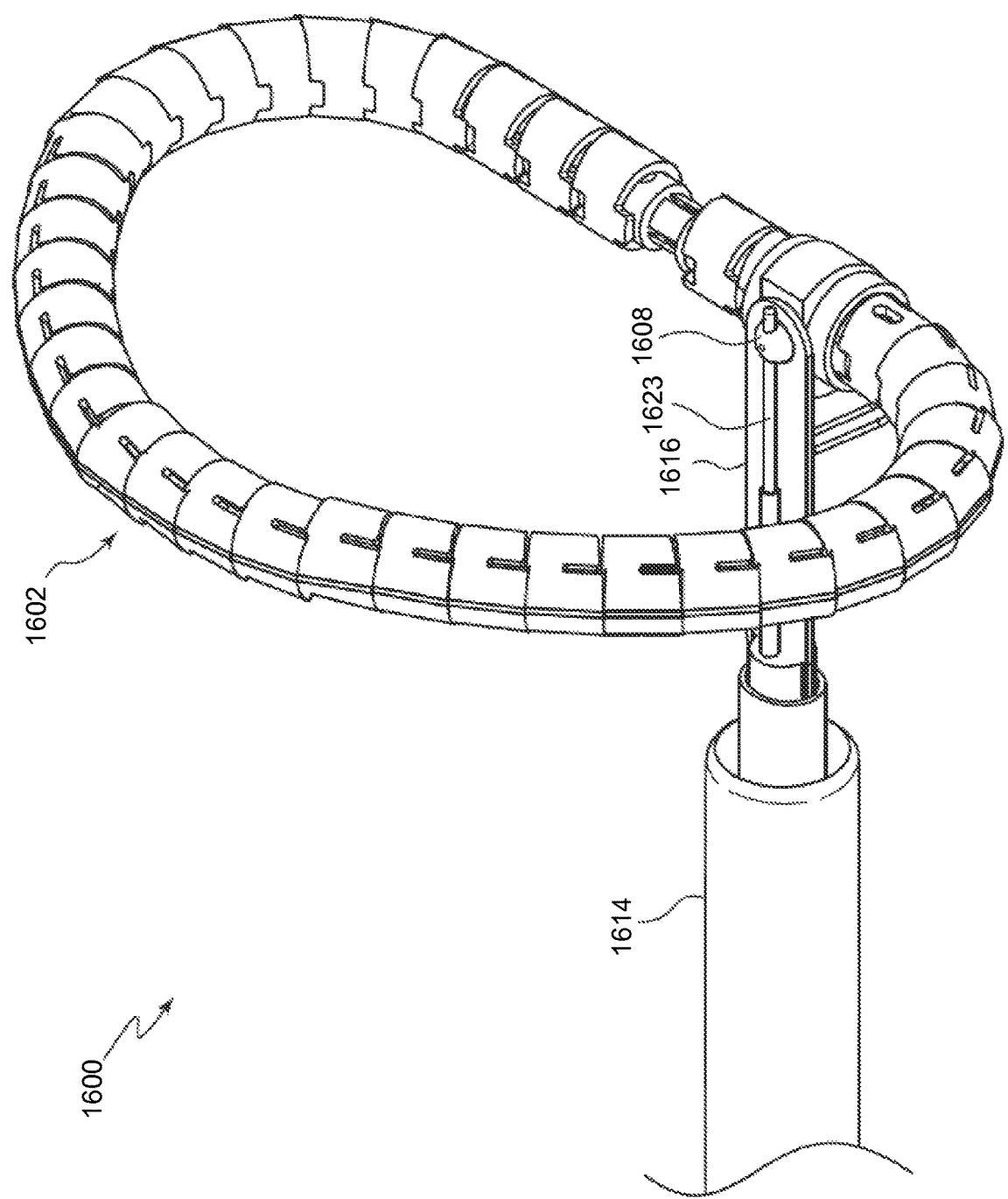
FIG. 16D is a perspective view of an annuloplasty ring 1602 in a fourth stage of deployment.

FIG. 16D is a perspective view of the annuloplasty ring 1602 in a fourth stage of deployment in which the plane of the annuloplasty ring 1602 (in its annular operable geometry) has been changed to be perpendicular to the longitudinal axis of the delivery catheter 1614. As shown in FIG. 16D, the superelastic ring deployment wire 1623 has returned to its heat set (memorized) straight configuration. At this fourth stage of deployment, the plane of the annuloplasty ring 1602 is configured to be parallel to the plane of the heart valve annulus. In situ within the heart, a longitudinal axis of the delivery catheter 1614 is oriented parallel to the direction of blood through the valve and approximately perpendicular to the plane of the heart valve. The annuloplasty ring 1602, when oriented such that the plane of the annuloplasty ring 1602 is transverse to (and perpendicular or approximately perpendicular to) the longitudinal axis of the delivery catheter 1614, is oriented such that the plane of the annuloplasty ring 1602 is parallel or approximately parallel to the plane of the heart valve.

In further stages of deployment, the annuloplasty ring 1602 may be expanded and/or pressed against the heart valve annulus before deploying the anchors (such as the curved anchors 104 shown in FIGS. 1A and 1B). As discussed above, certain anchor embodiments propel themselves into the tissue of the heart valve annulus upon being deployed. In other embodiments, the anchors (such as the linear anchors 1340 shown in FIG. 13) may be deployed before pressing the annuloplasty ring 1602 against the annulus. After the annuloplasty ring 1602 is anchored to the heart valve annulus and transitioned to the contracted state, the ring deployment wire 1623 may be pulled from the hole in the pivot 1608 to release the annuloplasty ring 1602 from the ring shuttle 1616. Any remaining sutures, such as the first suture 1619, may also be cut and/or pulled from the annuloplasty ring 1602 before the delivery catheter 1614 is removed from the heart.

Figure 17A:
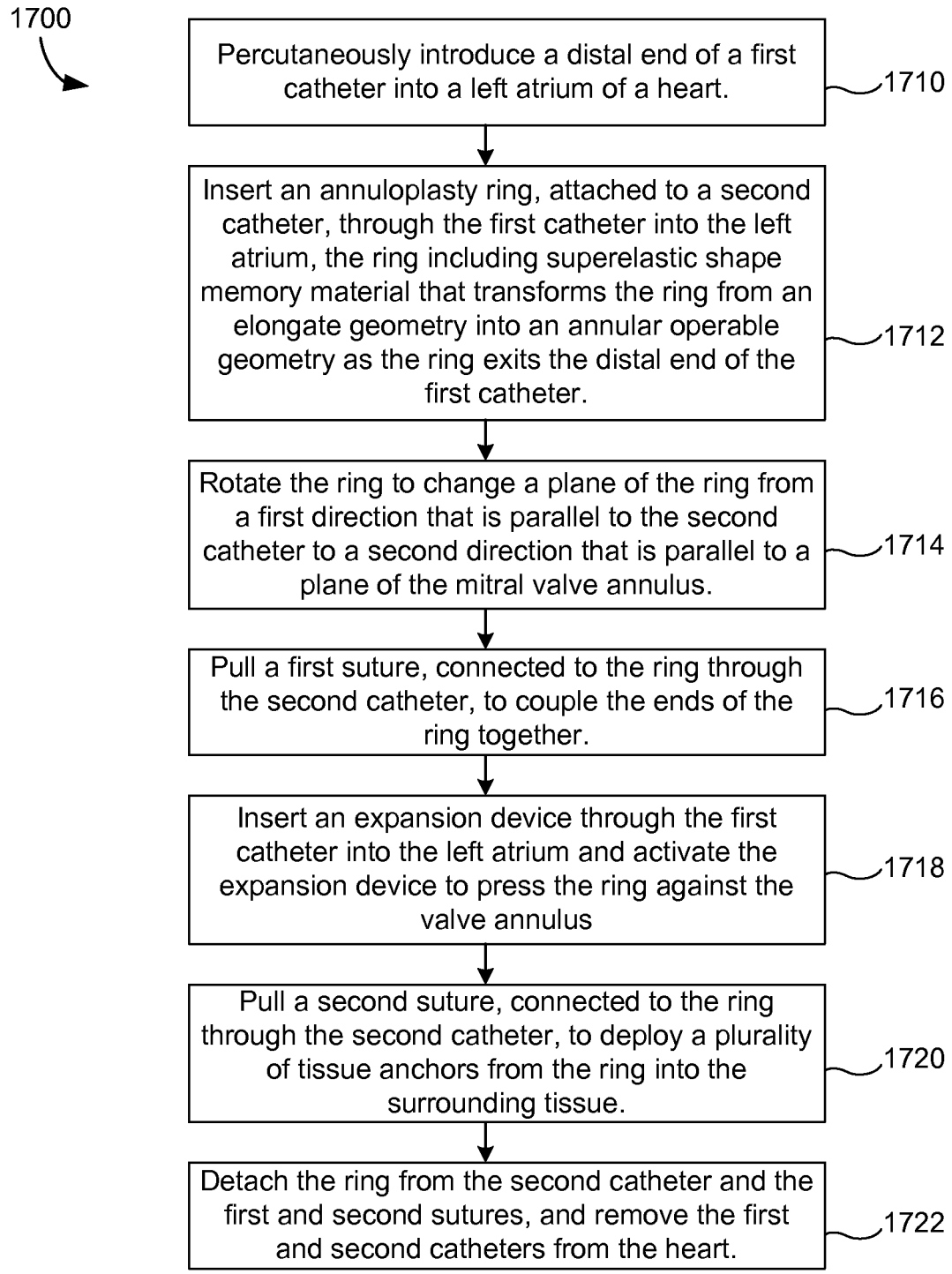
FIG. 17A is a flowchart for a method for repairing a defective heart valve according to certain embodiments.

FIG. 17A is a flowchart of a method 1700 for repairing a defective heart valve according to one embodiment. The method 1700 includes percutaneously introducing 1710 a distal end of a first catheter into a left atrium of a heart and inserting 1712 an annuloplasty ring, attached to a second catheter, through the first catheter into the left atrium. The ring includes a superelastic shape memory material that transforms the ring from an elongate insertion geometry to an annular operable geometry as the ring exits the distal end of the first catheter. The method 1700 further includes rotating 1714 the ring to change a plane of the ring from a first direction that is parallel to the second catheter to a second direction that is parallel to a plane of the mitral valve annulus, and pulling 1716 a first suture, connected to the ring through the second catheter, to couple the ends of the ring together. The method 1700 includes inserting 1718 an expansion device through the first catheter into the left atrium and activating the expansion device to press the ring against the valve annulus. Then, pulling 1720 a second suture, connected to the ring through the second catheter, to deploy a plurality of tissue anchors from the ring into the surrounding tissue. In some embodiments, the step 1720 of deploying anchors comprises retracting a retaining ribbon from across the anchors thereby causing the anchors to deploy as described above in relation to FIGS. 4A, 4B, 4C, 4D, and 4F. In other embodiments, the step 1720 of deploying anchors comprises rotating an inner tube within an outer cover thereby causing the anchors to deploy through windows in the outer cover as described above in relation to FIGS. 5A, 5B, 5C, and 5D. The method 1700 further includes detaching 1722 the ring from the second catheter and the first and second sutures, and remove the first and second catheters from the heart.

Figure 17B:
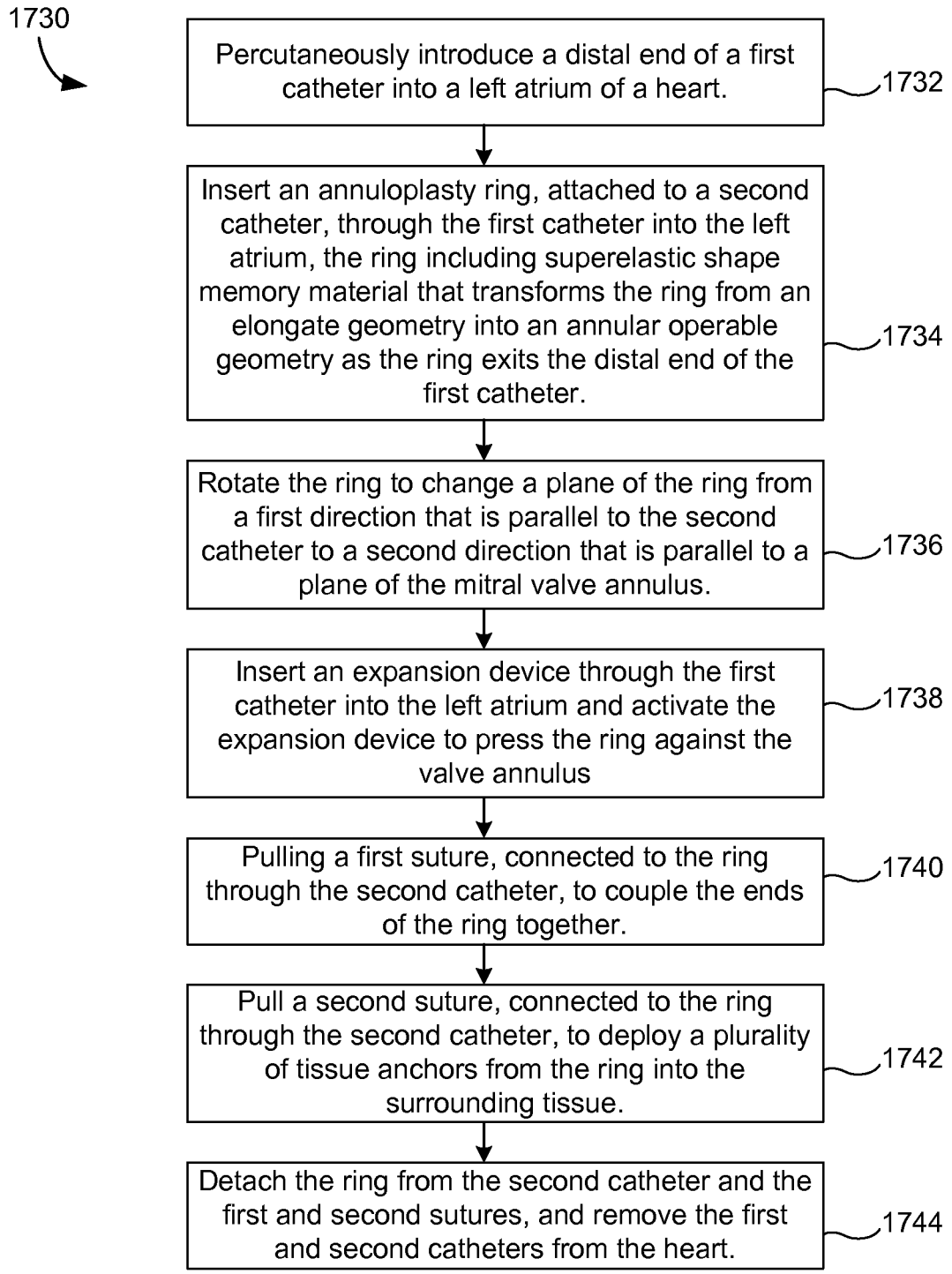
FIG. 17B is a flowchart for a method for repairing a defective heart valve according to certain embodiments.

FIG. 17B is a flowchart of a method 1730 for repairing a defective heart valve according to another embodiment. The method 1730 includes percutaneously introducing 1732 a distal end of a first catheter into a left atrium of a heart, and inserting 1734 a segmented annuloplasty ring, attached to a second catheter, through the first catheter into the left atrium. The ring includes superelastic shape memory material that transforms the ring from an elongate insertion geometry to an annular operable geometry as the ring exits the distal end of the first catheter. The method 1730 further includes automatically rotating 1736 the ring to change a plane of the ring from a first direction that is parallel to the second catheter to a second direction that is parallel to a plane of the mitral valve annulus, and inserting 1738 an expansion device through the first catheter into the left atrium and activating the expansion device to press the ring against the valve annulus. Pressing the ring against the annulus at this stage allows the subsequent deployment of the anchors to propel the anchors into the annulus tissue. Thus, the method 1730 further includes pulling 1740 a first suture, connected to the ring through the second catheter, to deploy a plurality of tissue anchors from the ring. Each of the plurality of anchors includes a superelastic shape memory material that propels the superelastic anchors into the tissue of the valve annulus. In some embodiments, the step 1740 of deploying anchors comprises retracting a retaining ribbon from across the anchors thereby causing the anchors to deploy as described above in relation to FIGS. 4A, 4B, 4C, 4D, and 4E. In other embodiments, the step 1740 of deploying anchors comprises rotating an inner tube within an outer cover thereby causing the anchors to deploy through windows in the outer cover as described above in relation to FIGS. 5A, 5B, 5C, and 5D. The method 1730 further includes pulling 1742 a second suture, connected to the ring through the second catheter, to couple the ends of the ring together and cinch the valve annulus to a desired size. The method 1730 also includes detaching 1744 the ring from the second catheter and the first and second sutures, and removing the first and second catheters from the heart.

Figure 18:
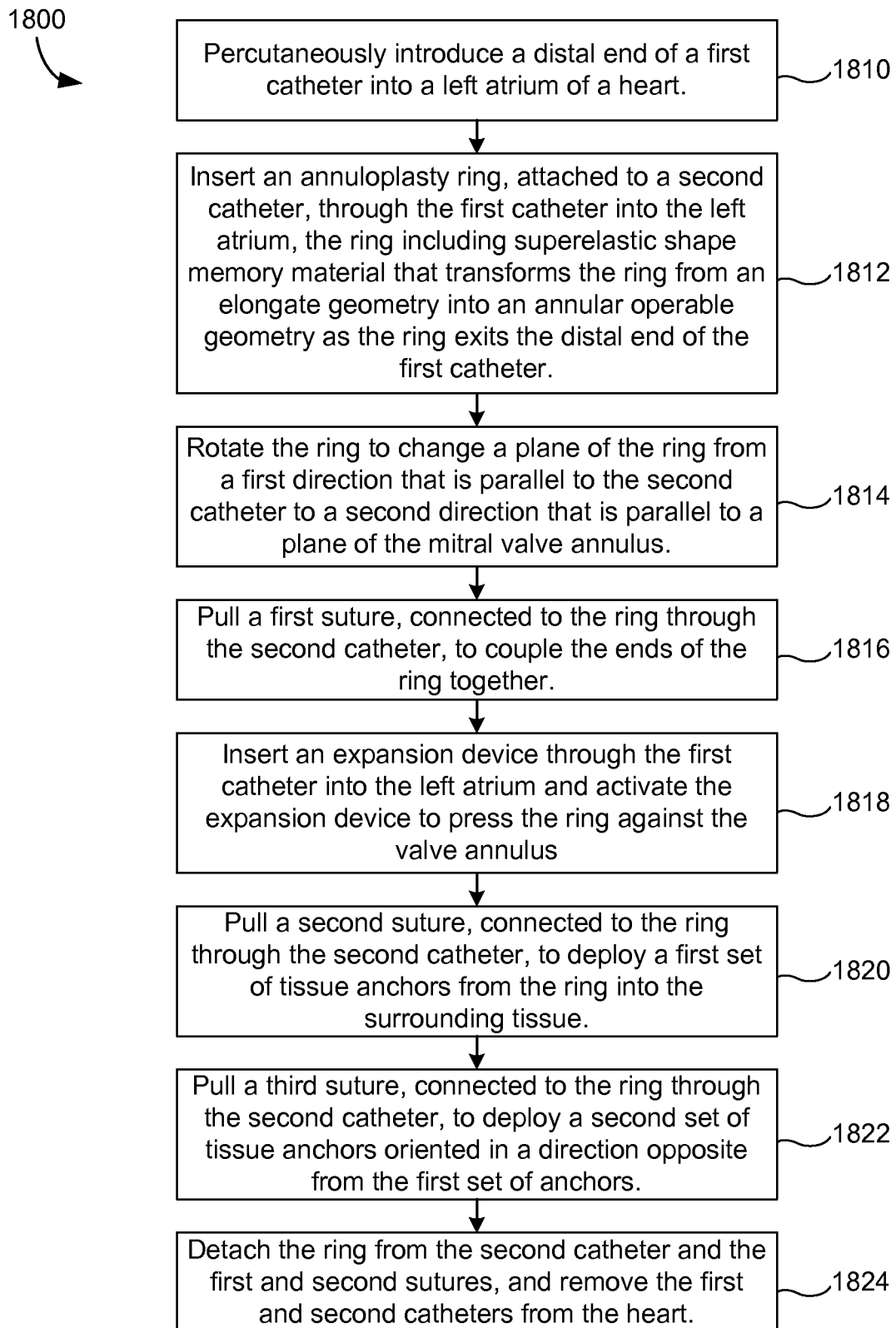
FIG. 18 is a flowchart for a method for repairing a defective heart valve according to certain embodiments.

FIG. 18 is a flowchart of a method 1800 for repairing a defective heart valve according to one embodiment. The method 1800 includes percutaneously introducing 1810 a distal end of a first catheter into a left atrium of a heart and inserting 1812 an annuloplasty ring, attached to a second catheter, through the first catheter into the left atrium. The ring includes a superelastic shape memory material that transforms the ring from an elongate insertion geometry to an annular operable geometry as the ring exits the distal end of the first catheter. The method 1800 further includes rotating 1814 the ring to change a plane of the ring from a first direction that is parallel to the second catheter to a second direction that is parallel to a plane of the mitral valve annulus, and pulling 1816 a first suture, connected to the ring through the second catheter, to couple the ends of the ring together. The method 1800 includes inserting 1818 an expansion device through the first catheter into the left atrium and activating the expansion device to press the ring against the valve annulus. Next, pulling 1820 a second suture, connected to the ring through the second catheter, to deploy a first set of tissue anchors from the ring into the surrounding tissue. The method includes pulling 1822 a third suture, also connected to the ring through the second catheter, to deploy a second set of tissue anchors oriented in a direction opposite (anti-parallel) from the first set of anchors into the surrounding tissue. The method 1800 may also include pulling additional sutures, also connected to the ring through the second catheter, to deploy additional sets of tissue anchors, located on additional anchor regions of the annuloplasty ring, into the surrounding tissue. In some embodiments, three sets of anchors are deployed; each set of anchors attached to an internal anchor ribbon and deployed using a separate suture. In addition, or in other embodiments, the method 1800 may also include pulling another suture, connected to the ring through the second catheter, to couple the ends of the ring together. The method 1800 further includes detaching 1824 the ring from the second catheter and the first, second, and third sutures, and remove the first and second catheters from the heart.

Those having skill in the art will understand from the disclosure herein that many changes may be made to the details of the above-described embodiments without departing from the underlying principles of the invention. The scope of the present invention should, therefore, be determined only by the following claims.

The invention claimed is:

1. An annuloplasty device for transcatheter heart valve repair, the annuloplasty device comprising:
   an outer tube comprising a plurality of windows, the outer tube including an axis along its length;
   an internal body member within the outer tube, the internal body member comprising a plurality of anchors; and
   an anchor deployment system to selectively rotate the internal body member about the axis of the outer tube, the rotation deploying the plurality of anchors through the plurality of windows.

2. The annuloplasty device of claim 1, wherein the anchor deployment system comprises a wire configured to percutaneously rotate the internal body member.

3. The annuloplasty device of claim 1, wherein the internal body member comprises a hollow passage and one or more tabs extending from a surface of the hollow passage, and wherein the anchor deployment system comprises:
   a rotation member configured to be pushed or pulled through the hollow passage of the internal body member by a line connected to the rotation member through a catheter, the rotation member to convert linear movement of the line through the catheter into rotation of the internal body member.

4. The annuloplasty device of claim 3, wherein the rotation member comprises:
   a threaded groove along an outer surface of the rotation member, the threaded groove to engage the one or more tabs and rotate the internal body member as the rotation member is pushed or pulled through the hollow passage.

5. The annuloplasty device of claim 1, wherein the plurality of anchors comprise a superelastic shape memory material configured to self-propel the anchors into tissue of a heart valve annulus when respective tips of the plurality of anchors are aligned with the plurality of windows.

6. The annuloplasty device of claim 5, wherein the plurality of anchors comprise:
   an introduction configuration for inserting the annuloplasty device through a catheter, wherein the plurality of anchors in the introduction configuration are curved in a first direction so as to be concentric with a surface of the internal body member with respect to the axis; and
   a deployed configuration for attaching the annuloplasty device to the tissue of the heart valve annulus, wherein the plurality anchors in the deployed configuration are curved in a second direction that is opposite to the first direction, a transition from the first direction to the second direction increasing a force of the superelastic material for driving the plurality of anchors into the tissue.

7. The annuloplasty device of claim 1, wherein at least one of the outer tube and the internal body member comprises a superelastic shape memory material configured to change from an elongate insertion geometry to an annular operable geometry, the annuloplasty device configured to pass through a catheter and into a heart chamber in the elongate insertion geometry.

8. The annuloplasty device of claim 1, wherein at least two of the plurality of windows are aligned on the outer tube to substantially simultaneously deploy at least two corresponding anchors of the plurality of anchors.

9. The annuloplasty device of claim 1, wherein at least two of the plurality of windows are aligned on the outer tube to selectively deploy at least two corresponding anchors of the plurality of anchors at different times.

10. The annuloplasty device of claim 1, wherein one or more of the plurality of anchors include a shape selected from a group comprising curved, wavy, straight, and curled.

11. The annuloplasty device of claim 1, wherein one or more of the plurality of anchors include a pattern cut therein to control at least one of strength and flexibility, the pattern selected from a group comprising a series of rounded rectangular cutouts, a plurality of wavy cutouts, and one or more slots cut along an anchor length.

12. An annuloplasty ring for transcatheter heart valve repair, the annuloplasty ring comprising:
  an outer hollow member configured to change from an elongate insertion geometry to an annular operable geometry, the outer hollow member comprising a plurality of windows;
  a first internal anchor member located at least partially within the outer hollow member, the first internal anchor member comprising a plurality of first anchors configured to attach the annuloplasty ring to tissue of a heart valve annulus, the first internal anchor member configured to move the plurality of first anchors with respect to corresponding windows of the plurality of windows in the outer hollow member to selectively deploy the plurality of first anchors through the corresponding windows; and
  a second internal anchor member located at least partially within the outer hollow member, the second internal anchor member comprising a plurality of second anchors configured to attach the annuloplasty ring to the tissue of the heart valve annulus, the second internal anchor member configured to move the plurality of second anchors with respect to corresponding windows of the plurality of windows in the outer hollow member to selectively deploy the plurality of second anchors through the corresponding windows.

13. The annuloplasty ring of claim 12, wherein the plurality of first anchors and the plurality of second anchors are configured to deploy at substantially the same time.

14. The annuloplasty ring of claim 12, wherein the plurality of first anchors and the plurality of second anchors are configured to selectively deploy at different times.

15. The annuloplasty ring of claim 12, wherein the plurality of first anchors curve in a first direction in a deployed configuration, and the plurality of second anchors curve in a second direction in the deployed configuration, the second direction being different than the first direction.

16. The annuloplasty ring of claim 15, wherein the plurality of first anchors are each adjacent to a corresponding one of the plurality of second anchors in the deployed configuration.

17. The annuloplasty ring of claim 16, wherein adjacent anchors deploy through a same window of the plurality of windows.

18. The annuloplasty ring of claim 16, wherein adjacent anchors deploy through separate, adjacent windows of the plurality of windows.

19. The annuloplasty ring of claim 12, wherein at least one of the plurality of first anchors and one of the plurality of second anchors include a shape in a deployed configuration selected from a group comprising curved, wavy, straight, and curled.

* * * * *